US006529617B1

(12) United States Patent
Prokoski

(10) Patent No.: US 6,529,617 B1
(45) Date of Patent: Mar. 4, 2003

(54) METHOD AND APPARATUS FOR POSITIONING AN INSTRUMENT RELATIVE TO A PATIENTS BODY DURING A MEDICAL PROCEDURE

(76) Inventor: Francine J. Prokoski, 5410 Colchester Meadow La., Fairfax, VA (US) 22030

( * ) Notice: Subject to any disclaimer, the term of this patent is extended or adjusted under 35 U.S.C. 154(b) by 0 days.

(21) Appl. No.: 09/706,618

(22) Filed: Nov. 6, 2000

Related U.S. Application Data

(62) Division of application No. 08/823,841, filed on Mar. 27, 1997, now Pat. No. 6,173,068.
(60) Provisional application No. 60/022,727, filed on Jul. 29, 1996, provisional application No. 60/028,385, filed on Oct. 15, 1996, and provisional application No. 60/028,387, filed on Oct. 15, 1996.

(51) Int. Cl.[7] ................................................. G06K 4/00

(52) U.S. Cl. ....................................... 382/128; 600/473

(58) Field of Search ................................ 382/115, 118, 382/128, 130; 600/473, 474, 475, 310, 427, 429; 128/922, 897

(56) References Cited

U.S. PATENT DOCUMENTS

| | | | | |
|---|---|---|---|---|
| 4,817,622 A | * | 4/1989 | Pennypacker et al. ...... | 128/664 |
| 5,163,094 A | | 11/1992 | Prokoski et al. | |
| 5,375,603 A | * | 12/1994 | Feiler ......................... | 600/474 |
| 5,417,210 A | * | 5/1995 | Funda et al. ................. | 600/425 |
| 5,519,208 A | * | 5/1996 | Esparza et al. .............. | 250/226 |
| 5,608,821 A | * | 3/1997 | Esparza et al. .............. | 250/226 |
| 5,865,829 A | * | 2/1999 | Kitajima ........................ | 606/3 |
| 5,910,816 A | * | 6/1999 | Fontenot et al. ............... | 348/65 |
| 6,119,033 A | * | 9/2000 | Spigelman et al. .......... | 600/426 |
| 6,233,480 B1 | * | 5/2001 | Hochman et al. ............ | 600/476 |
| 6,259,943 B1 | * | 7/2001 | Cosman et al. .............. | 600/429 |

FOREIGN PATENT DOCUMENTS

| | | | |
|---|---|---|---|
| DE | 44 21 237 | 12/1994 | |
| WO | WO 94/20875 | * 9/1994 | ........... G02B/27/22 |

OTHER PUBLICATIONS

Cross, J.M. et al., "Thermographic Imaging of the Subcutaneous Vascular Network of the Back of the Hand for Biometric Identification," Proceedings of the 29th Annual Intnl Carnahan Conf on Security Technology, Sanderstead, GB, Oct. 18–20, 1995, pp. 20–35, Sanson.

* cited by examiner

Primary Examiner—Joseph Mancuso
Assistant Examiner—Martin Miller
(74) Attorney, Agent, or Firm—Lawrence E. Laubscher, Jr.

(57) ABSTRACT

A method and apparatus for annotation of medical imagery to facilitate patient identification, diagnosis, and treatment is characterized by an imaging device for producing a first signal representative of sensed characteristics of the individual and a minutiae generator which receives the first signal and produces a second signal representative of minutiae of the individual, the minutiae corresponding to specific branch points of blood vessels of the individual. A minutiae data generator analyzes the characteristics of minutiae and produces a third signal representative of the characteristics which is stored in a minutiae database for each of the plurality of known individuals and their medical conditions. The minutiae and minutiae data may be used to annotate medical imagery to facilitate subsequent image comparison by providing standardized registration points and time-varying characteristics. A minutiae matcher pairs corresponding second signals and third signals from a current patient with those from a database record, and the paired signals are used to align the images and compare them. The minutiae analysis techniques of the invention can be used to identify medical patients, assist in the diagnosis of medical conditions, and detect and monitor the use of alcohol and drugs, including anesthesia.

4 Claims, 19 Drawing Sheets

FIG. 2c  Arteries to Brain: Schema
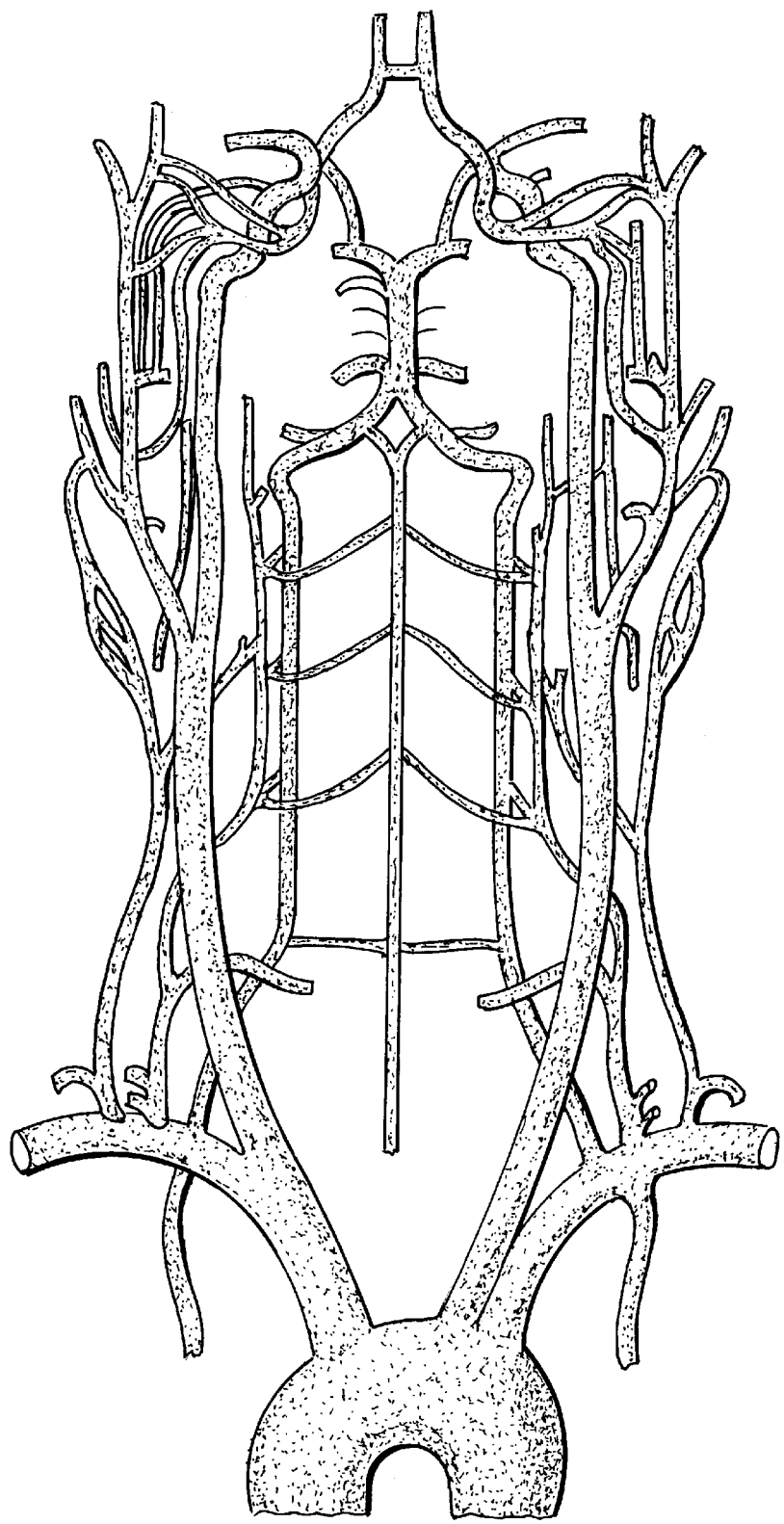

Facial Thermogram 200

THERMAL IMAGE FROM FIFTEEN FEET

FACIAL THERMAL MINUTIAE

FIG. 12
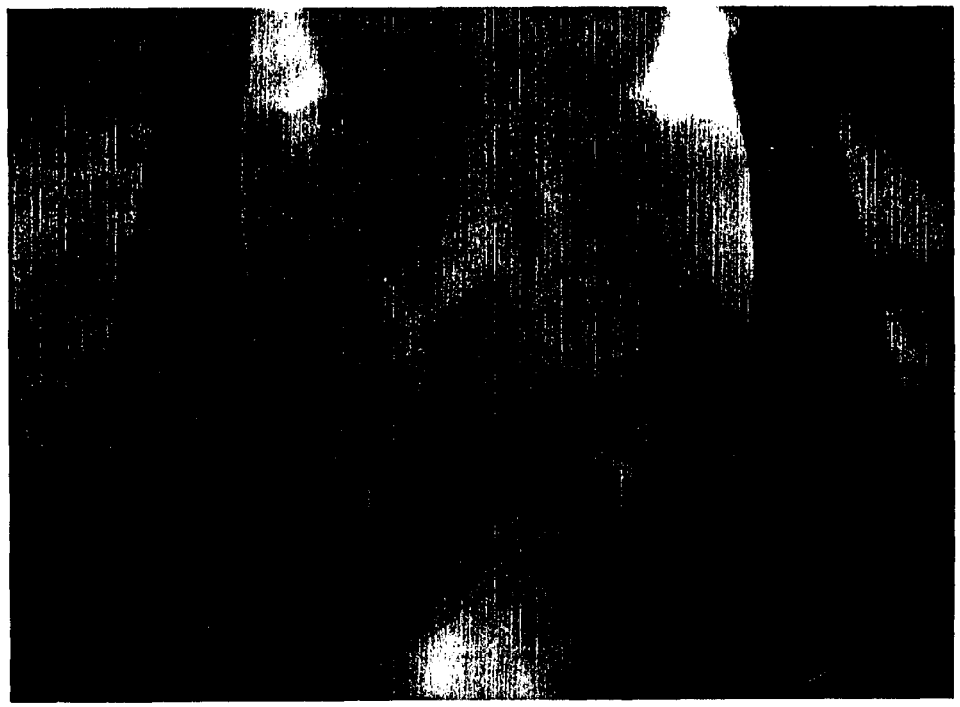
THERMAL CHEST IMAGE FROM FIFTEEN FEET
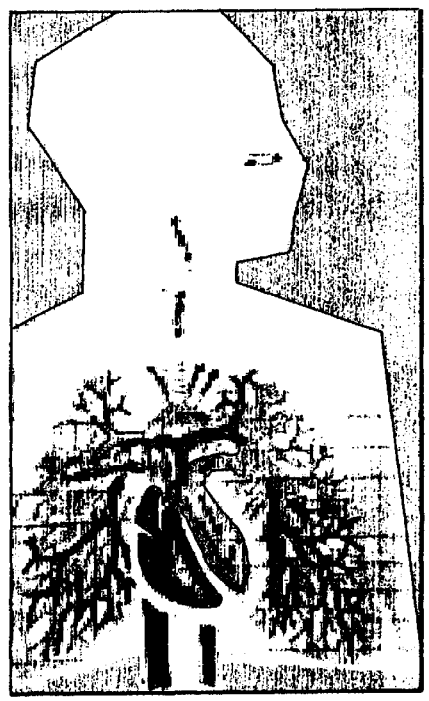
FIG. 13

Fran before and after alcohol

THERMAL MINUTIAE

METHOD AND APPARATUS FOR POSITIONING AN INSTRUMENT RELATIVE TO A PATIENTS BODY DURING A MEDICAL PROCEDURE

This application is a division of application Ser. No. 08/823,841 filed Mar. 27, 1997, now U.S. Pat. No. 6,173, 068, which application was based on provisional applications No. 60/022,727 filed Jul. 29, 1996, No. 60/028,385 filed Oct. 15, 1996 and No. 60/028,387 filed Oct. 15, 1996.

BACKGROUND OF THE INVENTION

This invention relates generally to the field of image recognition and processing and specifically to methods and systems for identifying, diagnosing, and treating people based on thermal minutiae within a person's body, primarily the face.

Improved methods for automated access control and surveillance are vital to ensure the continued security of nuclear weapon storage facilities, as well as other sensitive or valuable items. Potential threats range from terrorist bombings, insider thefts, and industrial espionage to sabotage by environmental activists. There is concern for increased vigilance in the protection of critical strategic assets.

Current technology being used for access control is not sufficient reliable, secure, fast rugged or cost effective for routine unattended operations at high-security locations. The challenge is to develop systems to secure facilities and personnel from internal and external threats in a cost effective and timely manner. Replacing human guards with automated systems can provide a significant cost savings.

The requirement to positively identify each individual seeking access to a facility or to information or services is widespread. Manpower-intensive guard brigades are deployed at public functions to protect celebrities, and at locations where valuable or important items are stored. Guards are used to screen entrants based upon recognizing either the person or some credential he carries. Identification credentials such as photo ID badges and driver's licenses are widely used for manual identification when cashing checks or using credit cards. Manual checking of such identification cards may not recognize cases where the card is forgery or where the person using it is not the rightful owner of the card. To assist in solving that problem, more sophisticated identifying characteristics may be used on the card, and features may be added to make the card more difficult to counterfeit. The use of biometric characteristics such as fingerprints, signatures, visual descriptions, or photographs is becoming more common. Such information can either be readable manually or encoded for reading by an automated system.

When the identification system is fully automated, without a human attendant, biometric sensors at the access location can compare the characteristics of a person at the location with the stored characteristics of the person he is claiming to be. When initially issuing permission for a person to access a biometrically-controlled system or location, his biometric characteristics are recorded in the system memory, and also recorded on an identification card, for later comparison by the system controller with his live characteristics.

BRIEF DESCRIPTION OF THE PRIOR ART

Current biometric identification systems include use of inkless fingerprint systems (called "live scan" units), retinal scanners, hand geometry measuring devices, voice recognition, handwriting recognition, and facial recognition systems which use either visual or infrared cameras. Use of fingerprints is generally considered the most secure method for positive identification. However, when used in the unattended mode, fingerprints can be lifted from one location or surface and positioned at another location. Therefore unattended use of fingerprints for identification at locations requiring very high security is not acceptable. A more common identification to widespread use of fingerprints for identification is the requirement for placing one or more clean fingers on a glass plate for imaging by the fingerprint recognition system. This requires that the hands be free and relatively clean, and that the glass plate be maintained intact and clean. The plates are vulnerable to vandalism. When used for access control at a busy location, there is a time delay associated with unloading the hands and positioning the fingers properly. Also, users must cooperate with the system. In certain scenarios of use, cooperation of the subject may be difficult to obtain. Furthermore, many persons have a reluctance to being fingerprinted for an identity card, since they associate the process with criminal activities.

Fingerprints traditionally have been the sole means of positive identification admissible as evidence in criminal trials in the U.S. Fingerprinting of criminals, military personnel, persons seeking security clearances, and persons applying for sensitive jobs has been performed for many years. The FBI established and maintained a card file in which each persons's fingerprints were printed by rolling the fingers first on an inked pad and then on the card. Much of the original FBI fingerprint file of rolled prints has now been digitized and made available on-line for computer access. The process of digitizing the historical files, and the continuing task of maintaining current fingerprint files, has cost hundreds of millions of dollars during the past ten years alone. Aside from the labor costs of performing the digitization and managing the search tasks through the database, significant R&D has been performed to develop specialized software for comparing unknown fingerprints against the database within a reasonable period of time, and specialized hardware has been developed to provide rapid response.

Inkless techniques are now generally used to produce a "tenprint" card which substitutes for the former rolled print card. Common inkless techniques utilize polarized light to illuminate the fingers, and light sensors to image the light reflected and refracted from the ridges. The resulting image can be more consistent and higher quality than the rolled prints, since inconsistencies in the amount of ink applied and in the pressure used to transfer the print to paper are not a factor.

Automated fingerprint matching techniques have been developed which rapidly classify an unknown print and then search through the portion of the database associated with that class looking for a match. Unknown prints may be from a "tenprint" card, or may be latent prints which have been lifted from a crime scene. A latent print may include a sizable area of one or more fingers, such as on a water glass, or it may include only a portion of one or more fingers, such as on a telephone keypad. Latent prints may be found on top of other latent prints, such as when several people been used the same telephone.

Matching techniques often extract minutiae points from the prints, and then compare the sets of minutiae rather than compare entire prints. Various classifications of minutiae types have been proposed by different companies and authorities. An example is given from the Costello U.S. Pat.

No. 4,947,443. Six types of "characteristic features" are presented in this patent, each one relating to a type of minutia. This fingerprint matching technique references the type, orientation, and location of each characteristic and each and every other characteristic. Using this approach, on the order of 80 to 150 minutia points are identified in each fingerprint. Other fingerprint minutiae extraction and matching patents produce essentially the same number of minutiae, with difference in what features of the set of minutiae are considered in attempted matching and in how the matching is performed. In U.S. courts, evidentiary rules have traditionally required that 16 or more minutia points be found to correspond between two prints in order for them to be considered to be from the same person. The determination of likely matching prints is generally, assisted or performed entirely by a computer system; however, the final decree of a match is made by a fingerprint expert, who reviews the computer system results.

Matches between different prints taken from the same finger are never perfect, since the fingers are deformable, three-dimensional, connected and jointed structures which leave two-dimensional prints on surfaces they encounter through pressure. The exact angles between the fingers and the surfaces, the amount and direction of pressure, and the effect of movement between the fingers and the surfaces all cause variations in the exact prints produced. Even when prints are produced by a live scan technique, variation in the lighting, hand position, oil or dust on the fingers, use of lotions, and scratches or paper cuts will produce mirror variations in the prints produced.

Therefore, the exact number, position, and characteristics of minutiae extracted from two prints may be different even though they are produced by the same finger. The challenge for an automated fingerprint identification system is to recognize allowable mirror variations in actual matching prints while not allowing variations so wide that mismatches occur. Several AFIS products are now commercially offered which provide acceptable accuracy. Local and regional police forces may use smaller databases which contain only the prints of persons historically associated with their areas, rather than relying on federal resources to search the entire nationwide FBI files. Smaller scale fingerprint system, such as those associated with a system which controls access to an office building, may use the same minutiae matching techniques.

With rolled and live-scan prints, the orientation of each print, and the finger to which it corresponds is known. Also, quality checks can be built into the process such that repeat prints may be taken to insure quality when needed. In the case of latents, however, the analysis is done after the fact. It is known which finger left the print, and the orientation of the finger may be in doubt when only a partial print is found. Therefore, matching of latents is much more difficult than matching of rolled or live scan prints.

Various minutiae extraction algorithms are used in current fingerprint identification systems, some of which merely utilize the location of the minutia points and others of which utilize also additional information about the type of minutia each point represents. For example, simple graph matching techniques can be used to compare the follow-the-dots vectors generated by connecting the minutia points in order forced by considering intersections with a spiral from the centerpoint of the fingerprint. Alternately, the ridge angle at each minutia point can be considered and matched along with the coordinates, in a best-fit attempt to match each unknown print to each known print. A measure of goodness of fit can then be computed and used to rank other possible matches.

U.S. Pat. No. 4,525,859 to Bowless teaches a pattern recognition system which detects line bifurcations and line endings, denoted minutiae, in a pattern of lines such as are found in a fingerprint. According to this reference, the FBI uses an automatic fingerprint identification system entitled "FINDER" which uses an optical scan reader. The information is then enhanced to eliminate grays and fill in gaps in the ridges. A 16×16 increment square window scans the fingerprint, an increment being a tenth of a millimeter. Thus, a window advances through the fingerprint in increments of tenth of millimeter and looks for ridges which enter the window but do not exit it. When such a ridge is identified, its coordinate location is stored and the ridge is analyzed to establish an angle, theta, of the ridge at the termination. The data are then re-scanned to look for terminations of valleys, which are ridge bifurcations. The additional coordinates and angles of each of the inverted ending points also are stored.

In latent points, the distances between ridges of a fingerprint average 0.4 millimeters but can vary by a factor of 2 for any individual finger depending on skin displacement when the finger contacts the hard surface normally encountered in establishing a print.

A known algorithm of the National Institute for Standard Technology can be used to compare a previously stored electronic image of minutiae coordinate locations with the minutiae locations identified and stored by the computer.

U.S. Pat. No. 5,040,224 to Hara discloses a fingerprint processing system capable of detecting a core of a fingerprint image by statistically processing parameters. Hara's invention provides a system to determine a core in the fingerprint image and/or to detect directions and curvatures of ridges of the fingerprint image prior to detection of the position of the core. This reference defines minutiae as abrupt endings, bifurcations, and branches.

U.S. Pat. No. 4,790,564 to Larcher teaches a process and apparatus for matching fingerprints based upon comparing the minutiae of each print in a database with precomputed vector images of search minutiae in a search print to be identified, comparing position and angle, a result of such comparison being a matching score indicating the probability of a match between the angle of a file print minutiae and the angle of precomputed vector images of the search minutiae. Over an under-inking of a rolled print can change the apparent type of minutiae associated with a particular point from one printing to the next. However, not all corresponding minutiae will appear to change type in the two pairs. Therefore, matching for type as well as for x and y coordinates provides a stricter match requirement and results in better system accuracy. Larcher assigns higher values to minutiae which match in x,y and type.

As Larcher points out, there are advantages to matching minutiae rather than the entire image of the fingerprint in itself. An elementary matching operation comprises the comparison of two sets of minutiae, i.e., two sets of points, each point having three coordinates x, y, and a. An elementary matcher attempts to superimpose the two sets of points, in order to count the number of minutiae which are common to the two fingerprints.

Numerous other schemes for matching fingerprints are known. For example, matches referred to in Wegstein, Technical Note 538 of the National Bureau of Standards (1970), as M19, M27, and M32, determine whether two fingerprints come from the same finger by computing the density of clusters of points in Dx-Dy space, where Dx and Dy are the respective differences in x and y coordinates for the minutiae of two fingerprints. Experimental results referred to in this reference indicate that in Dx-Dy space points tend to be located at random when coming from different fingerprints, whereas points tend to form a cluster when coming from fingerprints from the same finger.

In the M19 matcher, the assumption is made that the transformation needed to superimpose the two sets of minutiae points is a translation only. The M27 matcher is an M19 matcher with a new scoring function, intended to take into account greater translation displacements. The M32 matcher takes into account small rotations between two fingerprints in the following way: first an M27 matcher comparison is made between the two fingerprints; then, one of the two prints is rotated through "V" degrees from its original position and a new M27 comparison is made. All together an M32 matcher operation consists of seven M27 comparisons, corresponding to the following values for the angle V, i.e., V=−15, −10, −5, 0, +5, +10, +15 degrees.

Minutiae may be extracted manually or automatically. Automatic systems generally require better quality imagery. The matcher engine must allow for some degree of inaccuracy or variability with respect to each of the encoded coordinates due to human operator bias or precision limitations of automated feature extraction processes.

Larcher disclosed the use and comparison of type of minutiae, since there is a greater match accuracy when ridge endings are compared to ridge endings, and bifurcations to bifurcations, as opposed to comparing one ridge ending to one bifurcation.

Other known approaches compare two sets of image features points to determine if they are from two similar objects as disclosed for example in Sclaroff and Pentland, MIT Media Laboratory, Perceptual Computing Technical Report #304. This reference suggests that first a body-centered coordinate frame be determined for each object, and then an attempt be made to match up the feature points.

Many methods of finding a body-centered frame have been suggested, including moment of inertia methods, symmetry finders, and polar Fourier descriptors. These methods generally suffer from three difficulties: sampling error, parameterization error, and non-uniqueness. The technique used in Sclaroff and Pentman disclosure has the limitation that it cannot reliably match largely occluded or partial objects.

Known techniques associated with fingerprint minutiae extraction and matching can be summarized as follows:

First, an unknown finger is scanned optically:

Second, the image is divided into pixels, where the size of the pixel relates to the quality of the result desired;

Third, certain pixels are selected as minutiae points;

Fourth, each minutia is assigned a vector having magnitude and directional information in relation to the surrounding characteristics of the fingerprint. Typically for each fingerprint, there would be a substantial number of minutia vectors characterizing its image;

Fifth, the set of minutia vectors of the unknown print are compared by computer to the set of vectors of known prints; and Sixth, the comparison results are used to select potential matches and provide a goodness of fit indication between the unknown and known prints.

Numerous approaches to recognition using visible light imaging of faces have been proposed. Many of them apply standard pattern matching techniques, others involve definition of face metrics.

U.S. Pat. No. 4,975,969 to Tal discloses a method and apparatus for uniquely identifying individuals by measurement of particular physical characteristics viewable by the naked eye or by imaging in the visible spectrum. This reference defined facial parameters which are the distances between identifiable parameters on the human face, and/or ratios of the facial parameters, and teachers that they can be used to identify an individual since the set of parameters for each individual is unique.

Tal's approach utilizes visible features on the face, and therefore cannot be relied upon to distinguish between faces having similar visual features, for example as would be the case with identical twins. In addition, the "rubber sheeting" effect caused by changes in facial expression, the aging effects which cause lengthening of the nose, thinning of the lips, wrinkles, and deepening of the creases on the sides of the nose, all cause changes in the parameters and in ratios relied on in this method. Furthermore, the parameters and ratios of any particular person's face may be measured by anyone taking a photograph, and thereby used to select or disguise another person to appear to be that person. Therefore, the security provided by such a technique may not be adequate for unattended or highly sensitive locations.

Still another known scheme utilizes eigenanalysis of visual face images to develop a set of characteristic features. Pentland, View-Based and Modular Eigenspaces for Face Recognition, MIT Media Laboratory Perceptual Computing Section, Technical Report No. 245. Faces are then described in terms of weighting on those features. The approach claims to accommodate head position changes and the wearing of glasses, as well as changes in facial expressions. This disclosure teaches that pre-processing for registration is essential to eigenvector recognition systems. The processing required to establish the eigenvector set is extensive, especially for large databases. Addition of new faces to the database requires the re-running of the eigenanalysis. Accordingly, use of eigenanalysis may not be appropriate for use in a general face identification system such as would be analogous to the FBI's and AFIS fingerprint system.

Visible metrics typically require ground truth distance measurements unless they rely strictly upon ratios of measurements. Thus, such systems can be fooled by intentional disguises, and they are subject to variations caused by facial expressions, makeup, sunburns, shadows and similar unintentional disguises. Detecting the wearing of disguises and distinguishing between identical twins may be done from visible imagery if sufficient resolution and controlled lighting is available. However, that significantly increases the computational complexity of the identification task; and makes the recognition accuracy vulnerable to unintentional normal variations.

From the standpoint of evidentiary use, it might also be argued that the application of eigenanalysis to a very large database of faces, such as all mug shots in the FBI files, would be considered so esoteric by the public at large that automated matches based upon its use will not readily be acceptable to a jury as convincing evidence of identity. By comparison, techniques based on minutiae matching technique, such as are used with fingerprint identification, would be expected to find a more understanding reception by the law enforcement community, and to be more acceptable for evidentiary purposes within a reasonable number of years after their introduction.

One known scheme using facial thermograms for identification is described in the Prokoski et al U.S. Pat. No. 5,163,094 which discloses defining "elemental shapes" in the surface thermal image produced by the underlying vascular structure of blood vessels beneath the skin.

Depending on the environment of use, thermal facial identification may provide greater security over identification from visual images and may therefore be considered preferable. It is extremely difficult, if not impossible, to counterfeit or forge one face to look like another in infrared, whereas it is often possible to disguise one person to look like another in visible light. However, the use of elemental shapes is found in practice to be vulnerable to such variables as head rotation and tilt, ambient and physiological temperature changes, variations in imaging and processing systems, and distortions or obstructions in a facial image (e.g., due to eyeglasses).

Eigenanalysis of the elemental shapes of a thermal facial image has also been used for recognition. In one approach, several sets of elemental shapes are produced for each image by imposing different thermal banding constraints. The totality of shapes are then analyzed with respect to a library of facial thermal images. Eigenshape analysis is used to compare the characteristics of shapes in each person's images. Eleven characteristics of each shape are considered, including: perimeter, area, centroid x and y locations, minimum and maximum chord length through the centroid, standard deviation of that length, minimum and maximum chord length between perimeter points, standard deviation of that length, and area/perimeter.

Each person's image is then characterized by set of 11-coefficient vectors. The difference in eigenspace between any two images is calculated to yield a measurement to which a threshold was applied to make a "match/no match" decision. In practice, such a system yields a useful method and apparatus for some applications. However, the calculation techniques for such a system are computationally intensive and require additional computational analysis of the entire database when new images are added. As with others of the prior known techniques, recognition is seriously impacted by edge effects due to head rotation and tilt, and by loss of definition in very cold or very hot faces.

None of the known techniques for facial analysis is believed to be sufficiently robust and computationally straightforward to allow practical application of such a scheme for highly sensitive unattended security applications.

Therefore, the need remains for a system and method that can be used to reliably recognize and verify the identity of an imaged person without manual assistance and without cooperation from the person being identified.

SUMMARY OF THE INVENTION

In accordance with the present invention, a system for recognizing faces comprises a thermal imaging device, a minutiae generator, a minutiae data generator, and a minutiae matcher. The thermal imaging device produces a signal representative of the thermal characteristics of a new face. The minutiae generator is connected to the thermal imaging device and produces a signal representative of thermal facial minutiae of the new face. The minutiae data generator stores minutiae data corresponding to known faces. The minutiae matcher is connected to the minutiae generator and the minutiae data generator and compares minutiae of the new face and of the known faces, producing a signal representative of a match between the new face and one of the old faces.

In another aspect of the invention, a method of recognizing faces senses thermal characteristics of known faces, identifies minutiae of the known faces, senses thermal characteristics of a new face, identifies minutia of the new face, determines a distance metric from each of the known faces to the new face, and determines a match between the new face and one of the old faces based on the distance metrics.

In still another aspect of the invention, faces are classified according to thermal minutiae, and facial minutiae data are encoded as a number of bits by overlaying a grid of cells on a thermal representation of face, setting a bit to a first state if any minutiae are located within the cell corresponding to that bit, and setting the bit to a second state if none of the minutiae are located within the cell corresponding to that bit.

In yet further aspects of the invention, other imaging modalities are used, and other body parts or objects are used, for minutiae-based recognition. Techniques for identifying medical patients, diagnosing medical conditions, identifying drug and alcohol users, and assisting with the positioning of surgical instruments are also achieved with the present invention.

BRIEF DESCRIPTION OF THE FIGURES

Other objects and advantages of the invention will become apparent from a study of the following specification, when viewed in the light of the accompanying drawing, in which:

FIG. 2c is a schematic view of the vascular system of the human brain;

FIG. 12 is a thermogram of the upper chest area of an individual taken from a distance of approximately fifteen feet in accordance with the invention;

FIG. 13 illustrates the corresponding anatomy for the thermogram of FIG. 12;

DETAILED DESCRIPTION

Facial Minutiae Extraction

Figure 1:
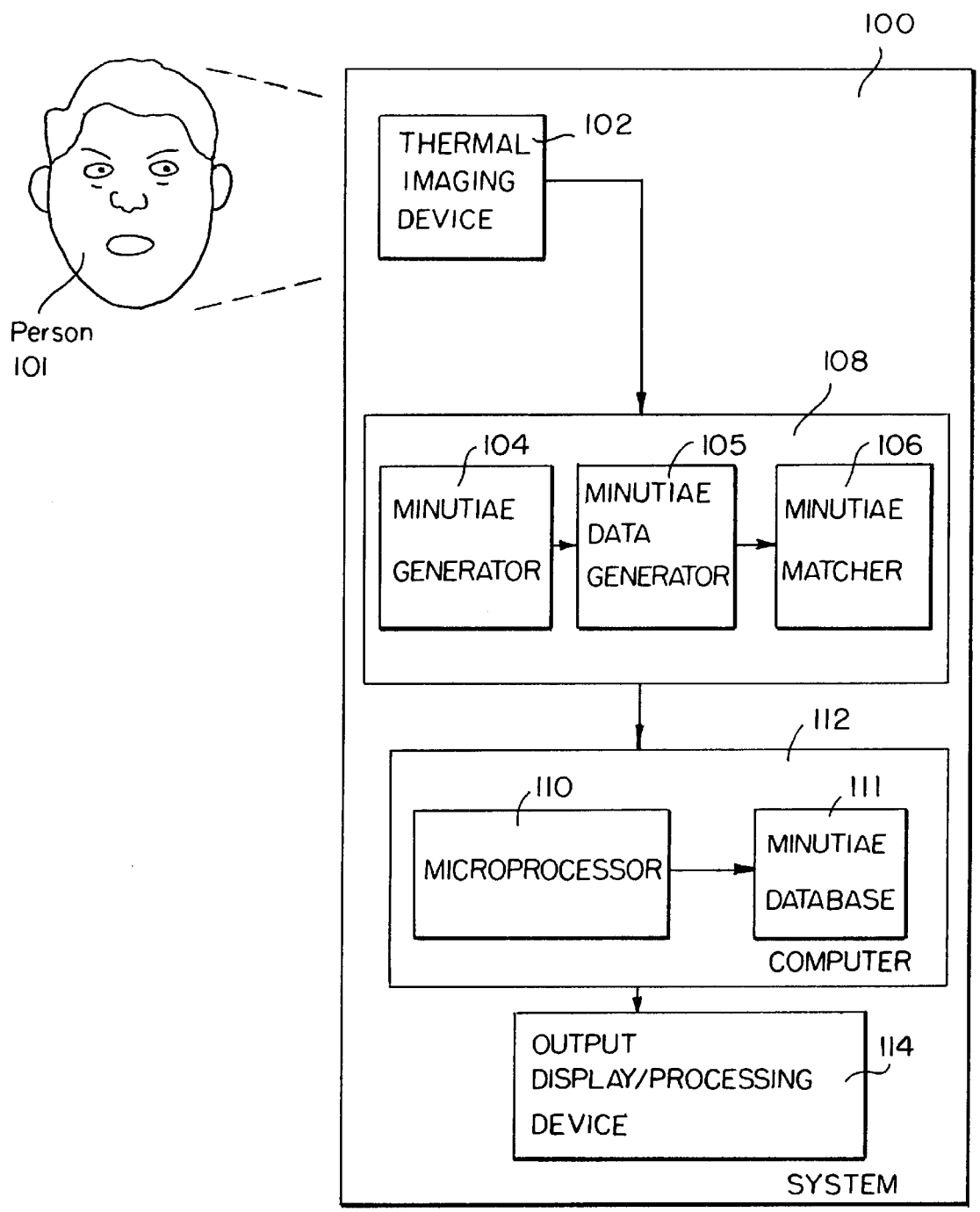
FIG. 1 is a block diagram of a system for recognizing faces according to the present invention.

In FIG. 1, there is shown a system 100 for personal identification in accordance with the present invention. System 100 includes seven major subsystems: a thermal imaging device 102, minutiae generator 104, a minutiae data generator 105, minutiae matcher 106, minutiae database 111, microprocessor 110, and output display/processing device 114. In a preferred embodiment, minutiae generator 104, minutiae data generator 105, and minutiae matcher 106 are all implemented by program instructions stored in a program memory 108, and program memory 108, microprocessor 110, and minutiae database 111 are implemented by a programmed conventional computer 112.

In operation, thermal imaging device 102 obtains a thermal image of the face of person 101. A digital signal representative of the thermal image is provided as input to minutiae generator 104, which generates signals representative of thermal facial minutiae points for 101. These minutiae points have a number of characteristics including a specific location within the person or relative to other minutia, the apparent temperature at a given time, the temperature signature over a period of time, whether the minutia corresponds to a vein or artery, the width of the blood vessel, and the vector direction of branching blood vessels from the minutia. These and other characteristics are sensed and data relative thereto are generated by a minutia data generator 105. This data is stored in the minutiae database 111. The minutiae matcher 106 compares minutiae data for known individuals which has been stored in the database with that for unknown individuals currently being imaged by the imaging device 102. If a match is detected, a corresponding signal is sent to the output display/processing device 114.

In a preferred embodiment, output display/processing device 114 comprises circuitry to permit or deny access to a secured facility depending on the results of the matching performed by minutiae matcher 106. In one embodiment, access is permitted if the person 101 is recognized as one of a group of authorized personnel. In a second embodiment, access is denied if the person 101 is recognized as one of a group of unauthorized personnel. In yet another embodiment, access is denied if the person 101 is not recognized by system 100.

System 100 thus considers hidden micro parameter which lie below the skin surface, and which cannot be easily forged, if at all. The large number of such micro parameters considered renders it essentially impossible to search for a person to match another person's set of micro parameters. Furthermore, the particular infrared band used for imaging by thermal imaging device 102 may be kept secret, or multiple bands may be used, which further increases the difficulty involved in compromising system 100. The underlying features detected by system 100 are essentially "hardwired" into the face at birth and remain relatively unaffected by aging, thus providing for less inherent variability than found in known recognition systems. Although thermal facial minutiae have some aspects related to, and extractable from, elemental shapes and may be tagged to reflect the elemental shape parameters (such as by tagging with fractal dimensions), minutiae extraction does not require production or consideration of elemental shapes. Furthermore, the comparison of thermal facial minutiae is computationally straightforward and introduces significantly less processing overhead than the known approaches used for template or shape comparisons.

Thermal imaging device 102 may be any device that produces a signal representative of the thermal characteristics of the face portion 101. In a preferred embodiment, a conventional digital video camera sensitive to thermal energy is used for the thermal imaging device 102. As described herein, it is found that tractable imagery for facial identification may be derived from passively obtained infrared images of facial heat emanations which can be detected by commercially available thermal imaging devices sensitive in the 3 to 12 micron wavelength band. Unlike fingerprints that are characterized by a limited range of intensity values corresponding to three dimensional ridges which are essentially concentric rings about a single center, plus anomalous arches, line endings, and bifurcations, facial thermograms are generally characterized by continuously varying wide distribution of temperatures, including multiple maxima and minima values. Where the skin surface is unbroken, there is gradual variation of temperatures from the hot areas on either side of the nose to the relatively cool areas of the ears and checks. The eyes appear to be cooler than the rest of the face. The nostrils and mouth, and surrounding areas, will look warm or cool depending upon whether the subject is inhaling or exhaling through them. Discontinuities in the skin surface temperature may be evident where scars, moles, burns, and areas of infection are found.

In some applications, thermal imaging device 102 may be adapted for attended operation using cooperative persons 101 and a human supervisor, as with identification systems based on rolled fingerprints. In these applications, the supervisor can ensure that person 101 is properly positioned, and can adjust gain, focus, and other parameter of thermal imaging device 102 to optimize the quality of the thermal image produced by thermal imaging device 102. In other applications, thermal imaging device 102 is adapted for unattended, stand-alone operation, for instance with live scans used for access control to a remote secure facility. System 100 can further be configured based on an expectation that person 100 will be either cooperative (e.g., moving to a specific requested location for optimal imaging) or uncooperative (e.g., a mere passer-by). In environments where uncooperative persons are expected, identification will be facilitated by collecting the maximum possible amount of data, for instance by using multiple thermal imaging devices 102 and fast frame (i.e., sampling) rates. Additional related data, referred to herein as "ground truth" data, may be collected as well to provide information on factors such as ambient temperature, absolute size of the imaged face, or the distance of the imaged face from thermal imaging device 102.

Figure 2A:
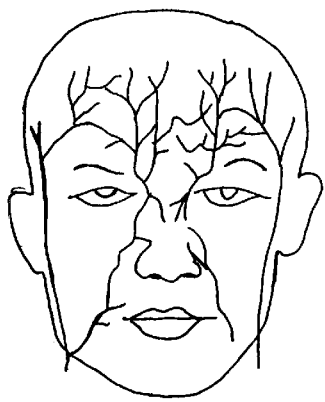
FIGS. 2a and 2b are front and side views, respectively, of the vascular system of the human head, with the location of thermal minutiae being indicated in FIG. 2b.

Any portion of the body can be utilized for identification, but the face is preferred due to its typical accessibility for imaging. In FIG. 2a there is represented the vascular system for a human face and in FIG. 2b there are shown minutiae points 150 for the face of FIG. 2a. In FIG. 3, selected minutiae points 150 throughout a human body are shown.

Since parts of the face may be blocked by glasses, facial hair, or orientation to thermal imaging device 102, system 100 provides for identification based on partial faces. A sufficient number of minutiae may be obtainable from portions of the face not blocked by glasses, facial hair, or other concealment, to permit matching. Alternately, if fewer than a minimum number of minutiae specified for a particular scenario are extracted by system 100 for a particular person 101 in an unattended setting, that person 101 may be considered by system 100 to be potentially disguised, and output/display processing device 114 may cause an alarm to be generated to alert guard personnel to that possibility.

Various perturbations, such as facial expression changes, can distort the relative locations of minutiae points. This is an analogous to the deformations that occur in fingerprints due to movement or pressure between the fingers and the print surface. As described below, minutiae matcher 106 allows for some variations in the position and characteristics of the minutiae, as well as in the subset of minutiae which are seen due to the field of view of thermal imaging device 102 and to possible obstruction of certain areas of the face in the image.

As set forth in greater detail herein, in one embodiment the minutiae database 112 is partitioned by classifying data corresponding to faces based on minutiae-related characteristics as generated by the minutiae data generator 105. In alternative embodiments, other characteristics may be used for such classification. Such classification is found to reduce search requirements in connection with the operation of database 112 and minutiae matcher 106.

Minutiae Generator 104

In a preferred embodiment, minutiae generator 104 performs seven major functions: designation of faces axes, testing of face axes validity; normalization; production of thermal contour lines; establishment of threshold radius of curvature; selection of minutiae; and assignment of characteristics to minutiae. Each of these functions is described in greater detail below.

I. Designation of Face Axes

Figure 4:
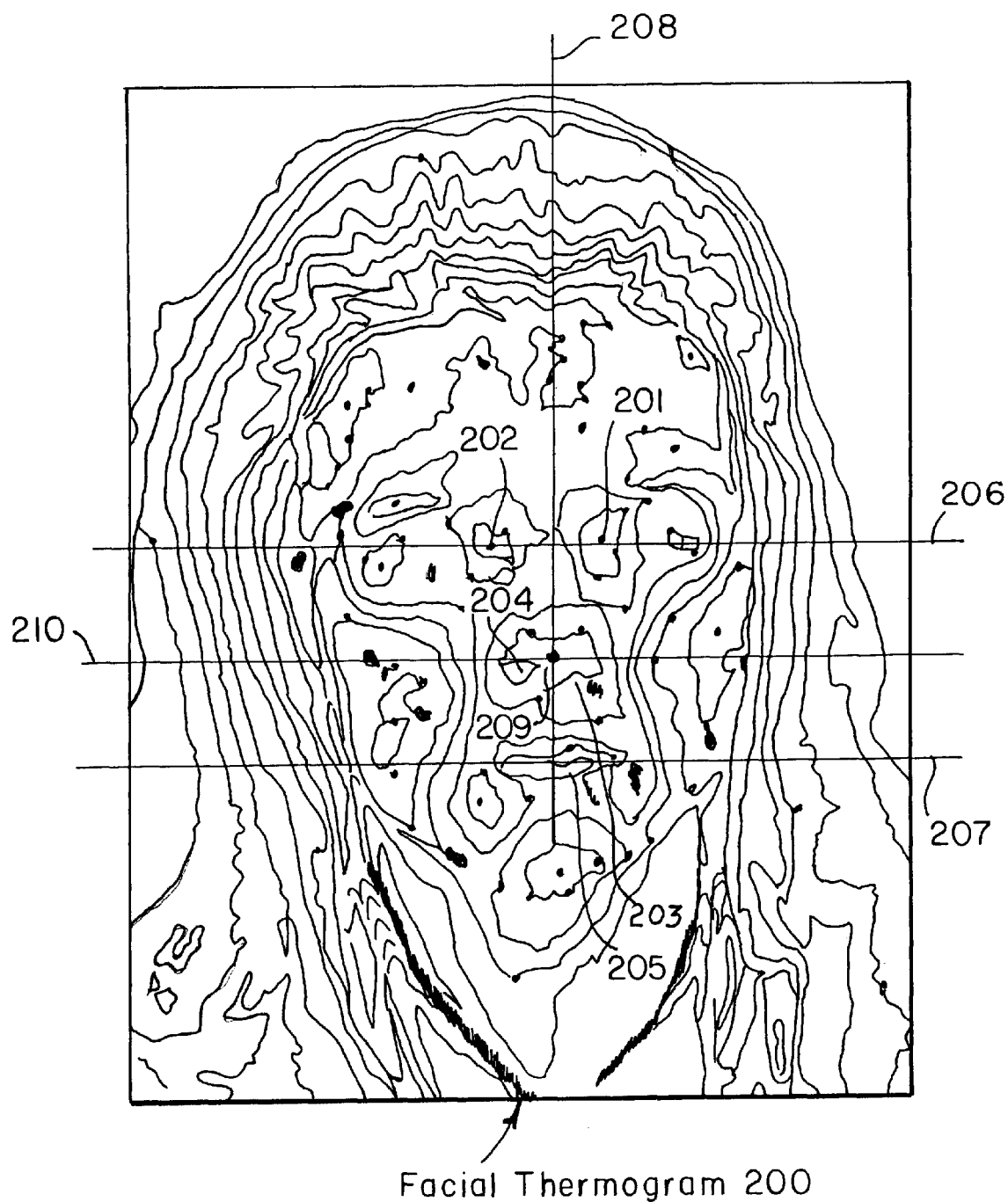
FIG. 4 illustrates a contour plot derived from a facial thermogram and identified facial features in accordance with the invention.

Referring now also to FIG. 4, there is shown a facial thermogram 200 as produced by thermal imaging device 102. The thermogram is in the form of a contour plot derived as set forth below. In a preferred embodiment, thermogram 200 produced by thermal imaging device 102 is represented by digital signals, but if an analog thermal imaging device 102 is used, minutiae generator 104 can include conventional analog-to digital conversion circuitry to obtain facial thermogram 200 as a digital signal representation of the face of person 101.

Once the facial thermogram 200 is produced, minutiae generator 104 locates a number of facial features on thermogram 200, either with manual assistance or automatically by using conventional techniques and structures as described herein: left and right canthi 201, 202, left and right nostrils 203, 204, and mouth area 205.

In a preferred embodiment, minutiae generator 104 locates the left canthi area and the right canthi area and determines the centroid for each area. The location of the centroid is essentially independent of the grey scale allocation of the analog thermal image produced by the camera 102. The centroids are referred to as left and right canthi 201, 202 herein.

Minutiae generator 104 also determines an eye line 206 between left and right canthi centroids 201, 202. This being done, minutiae generator determines a mouth line 207 parallel to eye line 206 and passing through the centroid of mouth area 205. Minutiae generator 104 next determines a vertical central line 208 perpendicular to eye line 206 and mouth area 205 and intersecting eye line 206 midway between left and right canthi centroids 201, 202. Minutiae generator 104 then determines a face center point 209 on central line 208 midway between the points of intersection of vertical central line 208 with eye line 206 and mouth 205. Minutiae generator 104 further determines a horizontal center line 210 perpendicular to the vertical central line 208 and passing through face center point 209. Vertical central line 208 and horizontal center line 210 are designated as face axes. Numerous other features may be used to define face axes, but in general it is preferable to define face axes based on areas of the face that are not greatly deformable.

Other techniques may be used for location of the face center point 209 in those cases where the preferred use of facial symmetry and recognizable thermal features does not suffice. For example, other techniques may be called for with respect to facial images in which an eye patch is worn, eyeglasses are not symmetrical, only a partial face is imaged, the lower face is covered, or the thermal pattern of the face is unusually distorted. The face center point 209 may in fact be outside of the boundaries of the facial image, for instance where only a partial facial image is obtained due to the face being partially blocked by another face or some other object. If the person 101 is wearing glasses, the pattern of the glasses, which typically block the infrared emissions from the face and thereby produce an extended cold area with sharp thermal discontinuity, can be used to determine approximate face axes. Additional techniques include manual location of the face center point 209 and preprocessing using known techniques to locate the approximate area of the face center point 209. As described below, the face axes may be tested for validity to determine whether the image requires any such special treatment.

II. Testing the Validity of Face Axes

Since the known techniques for identifying left and right canthi centroids 201, 202, left and right nostrils 203, 204, and mouth area 205 are subject to artifacts and other sources of error, and since some images of faces are significantly asymmetric or have features that are entirely missing (e.g., due to person 101 wearing an eye patch or having a disfigured face), minutiae generator 104 performs checks to help spot instances where these points may have been incorrectly located or where unusual facial images are encountered. First, a check is made to ensure that vertical central line 208 and mouth line 207 intersect within mouth area 205. Next, a check is made to ensure that vertical central line 208 intersects a line connecting left and right nostrils 203, 204 at point between left nostril 203 and right nostril 204. If either of these conditions is not met, the face is considered to be a special case calling for manual intervention to determine the best approximation for face axes.

III. Normalization

In practice, it is found that preprocessing through normalization of image size provides advantages in later recognition. Accordingly, minutiae generator 104 uses the distances between left and right canthi centroids 201 and 202 and the distance from face center 109 to eye line 206 to compare the size of facial thermogram 200 with a standard image size. In a preferred embodiment, linear correction in the vertical and horizontal dimensions is used to normalize the size of facial thermogram 200 to match the standard, but other normalization models could be used as well.

IV. Production of Thermal Contour Lines

As provided by thermal imaging device 102, facial thermogram 200 consists only of an ordered list of thermal values corresponding to each small portion of the imaged face. Minutiae generator 104 employs the following procedure to produce thermal contour lines for facial thermogram 200.

a. For a digitized image having N bits of resolution, or $2^N$ bands of thermal values, determine thermal contour lines having a particular "current" one of the $2^N$ values.

b. Produce minutiae in accordance with the steps below for the contour lines of the current value.

c. Repeat a and b above, each time using new one of the $2^N$ values for the "current" value, until the desired number of minutiae have been extracted of all of the possible values have been processed.

d. If the desired number of minutiae have not been extracted, repeat the process beginning with $2^{N-1}$ bands of values, and reduce the number of bands by 1 with each iteration, skipping those that are powers of 2, until the desired number of minutiae have been extracted or until no further reduction in bands can be achieved.

Various other techniques for generating contour lines may also be used, with the goal being obtaining a sufficiently large number of minutiae for unique recognition, without producing too many spurious minutiae. Spurious minutiae increase processing overhead without benefitting recognition. The number of thermal bands that will produce an appropriate number of minutiae is readily determined by trial and error for any particular application of system 100.

V. Establishment of Maximum Radius of Curvature

In a preferred embodiment, points on a thermal contour are considered minutiae if they form inflection points for the contour. However, to avoid artifacts resulting in too many minutiae being selected, only inflection points for curves below a threshold radius will be considered minutiae. Therefore, minutiae generator 104 selects a maximum radius of curvature to be used in determining minutiae, based on characteristics of system 100 such as the resolution of thermal imaging device 102, the lens used, the quality of the recording and processing system, the desired number of minutiae to be extracted, the desired sensitivity and vulnerability of the system to minor variations in thermal image, the accuracy of the three dimensional model for registration of the face image, and the magnitude of systematic and random errors.

VI. Selection of Minutiae

Since the face thermal surface can be distorted through changes in expression, activities such as eating and talking, tight hat and other clothing, sinus inflammation, and weight gain and loss, the minutiae points to be extracted must remain fairly constant in spite of such changes, or must be able to be filtered through those change. Section of minutiae as described herein provide minutiae well-suited to such factors.

Minutiae generator 104 selects minutiae from the facial thermogram 200 after preprocessing as described above by first positioning a circle of radius R on a thermal contour such that the contour intersects the circle, crossing it at two points and dividing it with equal area in each half. Next, this circle is moved along the contour for as far as the contour can continue to intersect the circle at exactly two points while maintaining an equal area on either side. If, in so moving the contour, a location is found where further movement would cause the contour to intersect the circle at only one point, the contour has ended, and the end point is designated as minutia point. This situation typically occurs only at the edge of a facial image and only rarely within the area of the face. If a location is found where further movement would cause the contour to intersect the circle at three or more points, there is an inflection point within the circle. It can be located by considering the slope of the contour within the circle relative to the face axes. The point of maximum change in slope is then designated as a minutia point. If a location is found where further movement would cause the contour to intersect the circle at no points, there is a small island area within the circle. The centroid of that island is designated a minutia point.

Figure 5:
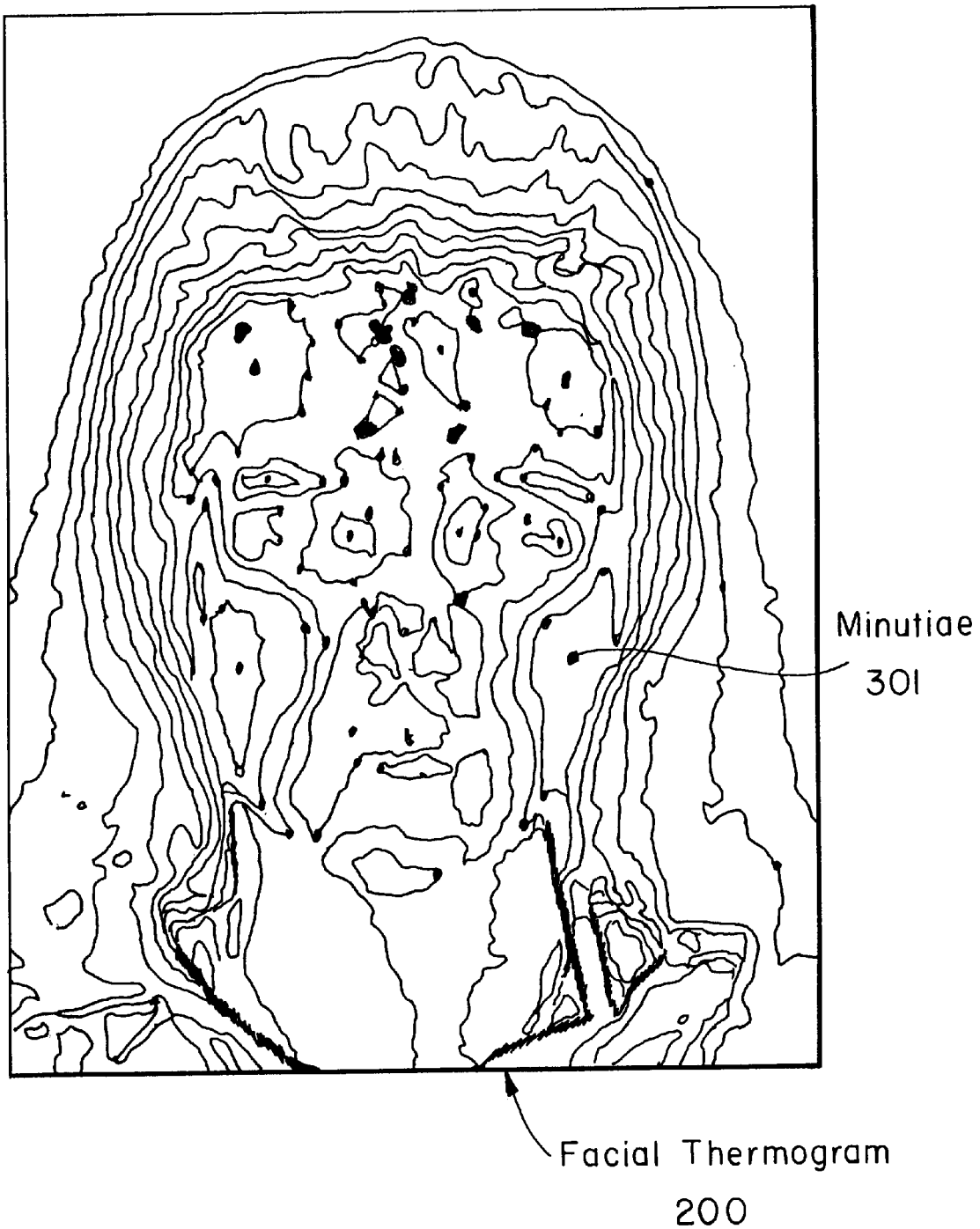
FIG. 5 illustrates a contour plot derived from a facial thermogram and minutia points in accordance with the invention.

Referring now to FIG. 5, there is shown a facial image on which minutia points, e.g, 301, have been identified on facial thermogram 200, as described above.

VII. Assignment of Characteristics to Minutiae

Once minutia points are selected, minutiae generator 104 assigns to each such point a label containing (s, y, z, α, R, B, T), where x and y are the horizontal and vertical displacements of the point relative to the facial axes, z is the thermal value of the point, α is the angle subtended by a tangent to the thermal contour at the minutia point, R is the radius as discussed above, B is the number or value of the thermal band in which the point is located, and T is the threshold imposed (if any) as discussed herein. In some environments, not all of these characteristics will be used and in such situations they need not be assigned. However, in some applications, these characteristics may advantageously be used for matching.

It should be recognized that numerous variation in the operation and structure of a minutiae generator could be used. For instance, minutiae that are simply centroids of areas of constant thermal values could be used. Depending on the resolution of the thermal imaging device 102, on the order of 300 thermal contours may typically be generated for a face, leading to 300 minutiae. This number of minutiae may be sufficient for identification purposes, depending on the application and environment in which system 100 is used. In some applications, it may be of interest to identify faces seen in crowds, or faces turned at any angle. Particularly in those applications, a significant number of minutiae points should be extractable so that even a partial face can be used for identification.

As another possibility, only centroids located near the center of the face, or in concave areas of the face less vulnerable to artifacts due to edges, could be used. In other applications, minutiae may be derived using centroids of images where all thermal values less than a threshold are maintained, but those higher values are collapsed in one band. Centroids may be added to the set as the threshold is reduced. In such instance, each minutia point is characterized using at least the (x, y, z, T) factors mentioned above, where T is the threshold. In a variation on this minutiae generation technique, inflection points produced from such thresholding rather than the centroids may be used.

Still another variation is to use start and stop locations from run length encoding of facial thermogram 200 to provide start and stop locations for thermal contours. Each stop/start location provides a minutia point which is characterized by the (x,y,z) values discussed above.

An additional approach is to designate undefined locations generated by compression and subsequent expansion of the image. Specifically, facial thermogram 200 is compressed using wavelet of fractal-based methods and then expanded again. Because such compression techniques are lossy in a deterministic way, a minutia set may be defined as the undefined locations resulting from a comparison of the original image with the compressed-and-expanded image.

This approaching provides an additional advantage of compressing the data used for recognition.

The wide variety of techniques for generating minutiae described above provides an added measure of security, as one attempting to mimic thermal facial minutiae may be able to do so if one technique for generating minutiae is used by minutiae generator 104, but not if another is used. Thus, without prior knowledge of the particular technique being employed by minutiae generator 104, system 100 becomes even more difficult to comprise than it otherwise might have been.

As mentioned above, it may be desirable that all thermal images be scaled to a standard size prior to processing. It also may be desirable, depending on the thermal imaging system used, that all thermal images first be normalized to a standard thermal profile before processing. In alternate embodiments, intended for various applications and various environments, these preprocessing steps may significantly increase accuracy in recognition or may merely impose unnecessary processing overhead. For example, if system 100 is used in connection with an outdoor automated teller machine, thermal normalization may be needed to deal with seasonally wide variations in surface skin temperature.

Minutiae Matcher 106

As mentioned above, minutiae generator 104 and minutiae data generator 105 are used to produce minutiae data signals for a population of known persons. The data corresponding to these signals are stored in minutiae database 112. Thermal imaging device 102 then obtains a thermal image of an unknown person 101 and minutiae generator 104 produces signals representative of the minutiae and minutiae data generator 105 generates data for the minutia for that person. Once these signals have been produced, minutiae matcher 106 compares the signals representative of person 101 to signals from minutiae database 102 corresponding to minutiae data of known persons. In a preferred embodiment, minutiae matcher 106 performs three basic functions to obtain a match: alignment of the unknown face, comparison of minutiae data, and selection of a match. Each of these functions is described in greater detail below.

I. Alignment of Unknown Face

Because there may not be control over the position of the face of person 101 with respect to the field of view of thermal imaging device 102 when image is obtained, the orientation of the face may not be such that the facial axes are aligned to be horizontal and vertical. Thus, minutiae matcher 106 corrects the orientation by rotating the image such that the facial axes are horizontal and vertical. Next, conventional processing using a three dimensional model is applied to correct for any rotation or twist of the head. In a preferred embodiment, such processing models the head as a sphere with a diameter equal to the apparent width of the face, and anti-distorts the image to provide a view which is normal to a surface plane across the forehead and upper lip and in which the enter of the sphere conincides with the face center. In a conventional manner, the nose and chin are ignored so as not to disrupt positioning of this surface plane.

II. Comparison of Minutiae

Comparison of the minutiae data of the unknown person 101 with minutiae data from known persons begins by comparing locations of such minutiae. First, the locations of minutiae for a known face are considered, and denoted as $M(K)i$. Next and allowed positional error $\epsilon$ of one of the $M(K)i$ are ignored. Any $M(K)i$ which are not within $\epsilon$ of on the $M(U)j$ are ignored. This leaves a residual set of minutiae pairs. If this set is empty, there is not a match between the two images. Otherwise, the characteristics of the corresponding points are compared.

Depending on the application, any comparison technique that considers the characteristics ($x, y, z, \alpha, R, B, T$) listed above may be used to generate a comparison metric. In a preferred embodiment, only the positional differences are considered.

The simplest decision technique is to set a minimum number of pairs of corresponding minutiae for a potential match. If an unknown face and a known face exhibit a least the minimum number of corresponding minutiae pairs, they are considered to be a potential match.

In an alternative embodiment, the $\Delta x$ and $\Delta y$ values for each pair of corresponding minutiae are determined, and the distribution of $\Delta y$ with respect to $\Delta x$ is then determined for the overall set of minutiae pairs. The standard deviation of that distribution is then compared against a threshold standard deviation to determine whether a potential match exists.

In still another technique, a new error measure $\epsilon'$ is introduced dependent not only on location but on thermal value ($z$). Minutiae pairs are only considered if they are within a certain thermal value difference $\Delta z$ as well as have locations within the distance error $\epsilon$, thereby satisfying new error measure $\epsilon'$.

Further levels of decision requirements can similarly be added to produce the desired level of confidence in the match for the application at hand. Each possible comparison of the unknown face with known faces is performed, and then the known images are rank-ordered according to the goodness to fit (e.g., closeness in metric) with the unknown face.

III. Selection of a Match

Through experience with use of the system on new images of known persons, a threshold value is established to provide a desired ratio of false positive and false negative identifications appropriate to the particular application. In a preferred embodiment, both self-correlations of multiple images of known persons and cross-correlations of different known persons in the database are used to help establish this threshold.

If only one known person meets the threshold requirement, that person is selected as the match. If no known person meet the threshold requirement, a failure to match signal is produced. If multiple known persons match the unknown person to within the threshold difference, the best matching person is selected. Alternatively, if multiple images of the same known person are referenced in minutiae database 112, the person having the highest ratio of matches within the top number of best matches may be used. For instance, if there are ten images of each known person in database 112, the top ten matching images determined by minutiae comparison are considered. The person who is associated with the most of the top ten is selected to be the matching person. Additional levels of decision requirements may be added, either in a simple manner or iteratively, with a determination after each level as to whether a match decision can yet be made.

In an alternative embodiment, minutiae matching is performed using techniques disclosed in U.S. patent application Ser. No. 07/984,514, filed Dec. 2, 1992, and U.S. Pat. No. 08/314,729, filed Sep. 29, 1994, which is a continuation of U.S. patent application Ser. No. 07/984,514, both of which are hereby incorporated by reference in this application as if the entire contents of each had been fully reproduced herein. In this alternative embodiment, flash correlation is used to match minutiae through a digitized artifact-producing technique. In this embodiment, the size of a minutia point is preferably increased to represent the possible error in its location, and minutiae are replicated successively along the face axes to increase their density and thereby increase the discernability of the correlation artifact that indicates a match between two images being compared. Such artifact is found to occur if any only if there is a match between two pixelized images.

Other known matching techniques may alternatively be used in minutiae matcher 106, with tolerances established for errors due to imperfect knowledge of head position or distance, errors introduced by considering the head or face as a two dimensional surface or as a sphere, and other systematic and random residual errors. Some known fingerprint matching techniques may also be adapted to use with minutiae matcher 106. By analogizing thermal contour to fingerprint ridges, the multiplicity of facial thermal contours may be treated in a manner similar to matching many fingers per person. Alternatively, specific areas of the face, such as surrounding the canthi, may be selected and used alone for identification. Depending on the resolution of the thermal imaging device 102, several hundred minutiae may be extracted from a facial thermal image. As noted above, lack of prior knowledge of which facial features, and which specific matching techniques are used for any particular application by system 100 increases the security of system 100 against being compromised by third parties.

For applications of system 100 to environments where legal proof of identification is important, a classification scheme for faces may be useful, as fingerprints traditionally have been classified into various classes for such applications. For example, whorls, arches, and loops are conventional descriptions applied to ridges in the center of a finger.

Another approach to classification of facial thermograms relates to obvious characteristics for use in verbally describing a given facial thermogram. Such characteristics include whether the canthi are merged or separated; whether the thermal contour of the nose is relatively cold, hot, or normal; whether the nose is trapezoidal in shape or irregular in shape; the degree of thermal symmetry of the forehead; and the degree of symmetry in location of thermal features in the mouth corners, the inner curves of the cheeks, the nose, the canthi, and the outer corners of the eyes. To be useful, such designations should remain consistent over variations in imaging equipment, environmental conditions, physiological variables, and other sources of errors. Accordingly, classification should not rely on features determined to be highly sensitive to such factors. Classifications based on overall image, e.g., those based on some of the distances between the features discussed in connection with FIG. 4 may be suitable for use.

Another approach is to use wavelet coefficients that produce the minimum difference between an interpolated wavelet-compressed image and the original image. Depending on how many classes are desired, that number of wavelet coefficient sets can be generated. Each image to be classified is compressed and then restored using each of the sets. The image is assigned to the class corresponding to the set of wavelet coefficients which best restores the image to its original form.

Figure 6:
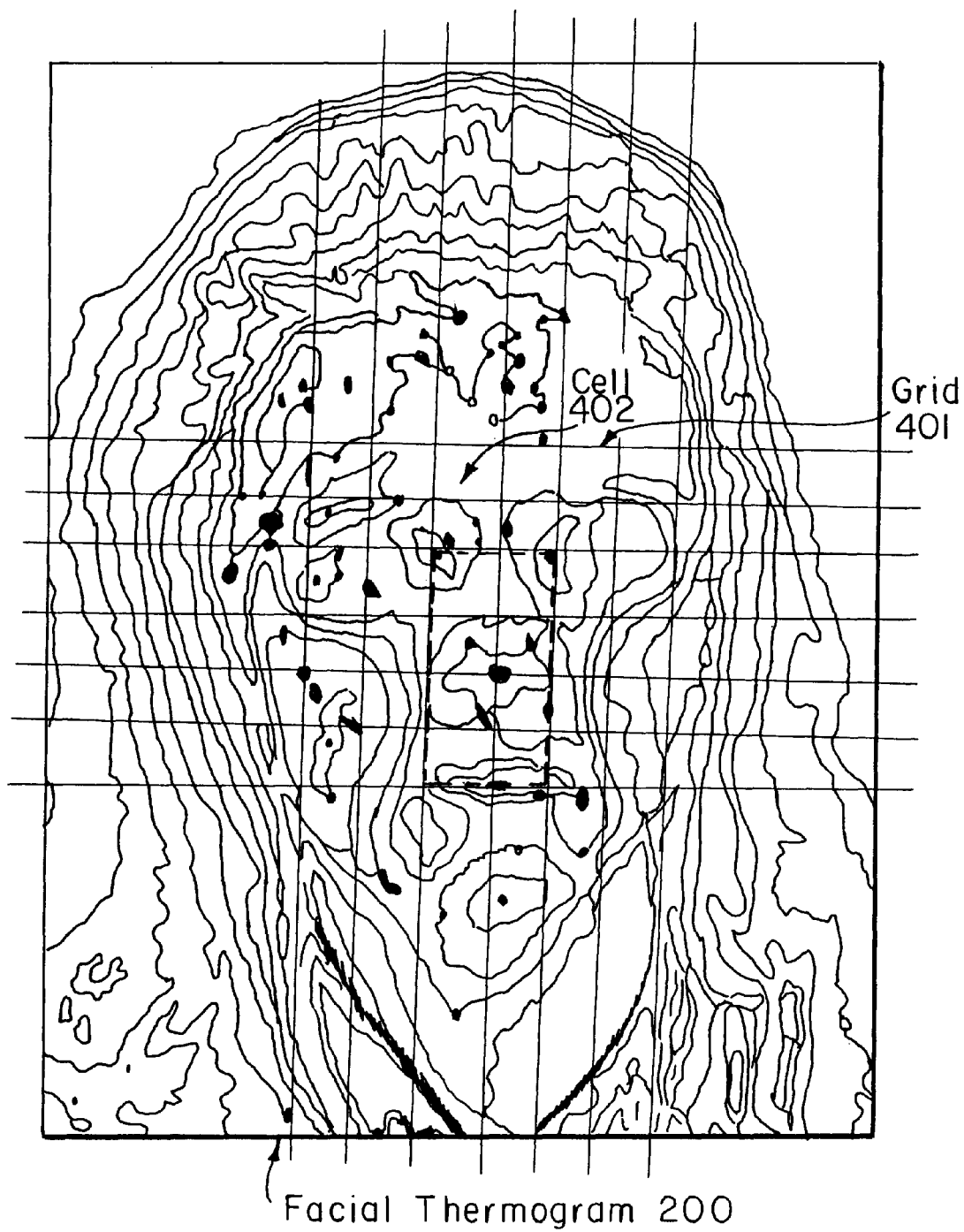
FIG. 6 illustrates a grid of cells overlaid on a contour plot derived from a facial thermogram in accordance with the invention.

Referring now to FIG. 6, classification of faces is achievable based on the number of minutiae, their characteristics, and their distribution over the face. A preferred classification method segments the face represented by thermogram 200 into a grid 401 of cells 402. Each cell is then classified based on the number of minutiae located therein. As an example, the facial thermogram 200 of FIG. 6 is divided into a grid 401, the cells 402 of which might be characterized as type A if the cell contains less than 3 minutiae, type B if the cell contains between 3 and 5 minutiae, and type C if the grid contains more than 5 minutiae. A face can then be classified based on the number of cells of each type that are found. For instance, one classification scheme is based on the number of type A and type C cells. If a face is divided in to 36 grid cells as illustrated in FIG. 6, classes could be designated as nAmC, where n is the number of type A cells m is the number of type C cells, n+m=36−p, and p is the number of B cells. Using this arrangement, 1260 classifications are possible. Alternatively, ranges of values can be considered to be within the same class.

As a further refinement to such classification, the degree of bilateral symmetry in distribution of type A cells and type C cells could be considered. If the face is divided into four quadrants designated upper right, lower right, upper left, lower left, each quadrant having 9 cells, a metric for classification could look at differences in the numbers of type A and type C cells in horizontally or vertically adjacent quadrants. Such metrics may be the absolute difference in minutiae between such quadrant pairs, or may be simplified by merely indicating whether a left (or upper) quadrant has more, fewer, or equal minutiae as a corresponding right (or lower) quadrant.

Other possible classifications are based on geometric values of, and ratios among, the points and lines described in connection with FIG. 4, once the face has been normalized as described above. In some applications, a combination of visual and thermal attributes may be employed for classification. For example, a ratio between the distance between left and right canthi centroids 201, 202 is facial thermogram and the distance between the left and right pupils as determined through visual imaging is found to be a useful metric for classification, as is the ratio between the distance from eye line 206 to horizontal central line 210 and the distance from a line connecting the eyes to the tip of the nose as determined by visual imaging, as is the ratio between the distance left and right nostrils 203, 204 and the distance between the outer limits of the nostrils as determined by visual imaging.

The usefulness of facial thermal imaging in recognition applications is increased by appropriately encoding thermal facial images so that consistent codes are generated each time a facial thermogram of a person is obtained. Such a coding scheme reduces database search and minutiae matching overhead, thereby allowing faster processing using less expensive equipment. In a preferred embodiment, overlaying a grid on a face such that 144 cells cover the area of the face, and assigning a binary code to each cell, such t hat the cell is encoded with a "1" if the cell contains one or more minutiae and "0" if the cell does not contain any minutiae, is found in practice to yield good results. Since this encoding scheme preserves the relative location of each bit, it is straightforward to ignore selected bits in cases where only a portion of a face is imaged, due to obstruction, disguise, or orientation.

Use of such a "facecode" also facilitates straightforward verification and comparison techniques. In some verification applications, for example, a requirement that 10% of the coded bits match may be considered sufficient to provide a desired level of confidence. Simple difference comparison on a bit-by-bit basis, which is computationally extremely efficient, is sufficient to determine the number of corresponding bits between a code of an unknown face and that of a known face. Where multiple known faces exceed a threshold level of similarity, the one with the greater number of common bits is readily selected as a best match.

Although the discussion above has been directed to thermal images of faces, it should be recognized that similar techniques and systems may readily be applied to images of other body parts in accordance with the present invention. It should also be recognized that numerous other imaging modalities besides thermal imaging may be employed in accordance with the present invention, for example x-ray, NMR, MRI, and CAT scan imaging. It should also be recognized that known schemes for pattern recognition and graph matching may be applied readily in accordance with the present invention, depending on the needs of a particular application.

Standardized Infrared Minutiae Co-Ordinate System (SIMCOS)

Figure 7:
FIG. 7 is a facial thermogram taken from a distance of approximately fifteen feet in accordance with the invention.

The method and apparatus described above for facial minutiae extraction can be used to develop a standardized minutiae co-ordinate system for identification of medical patients and for diagnosis of medical conditions. Because an infrared camera operates at a distance from the patient and detects and records only radiant heat spontaneously emitted from the body surface, it constitutes a painless, non-invasive, passive method of recording patterns of body surface temperatures. These patterns have been found to depend upon the underlying vascular structure and are unique for each person. Infrared identification therefore provides a method for uniquely identifying individuals under all lighting conditions, including total darkness. It is not prone to forgery or multiple identity deception and so provides convenient and highly secure identification of individuals. The method for generating repeatable registration points on the skin surface of the human body utilizes discrete minutiae points obtained from the thermal images. Visual characteristics of the body, such as size and shape and relative position of body parts, are maintained in the infrared image. In addition, the details of the vascular system are indicated by the distribution of temperature cross the skin surface. Current infrared cameras are sufficiently sensitive to temperature variations that they clearly distinguish the skin directly overlaying blood vessels due to the thermal difference caused by the flow of warm blood. The vascular structure appears as a white (hot) overlay of the circulatory structure on top of a grey scale image of the thermal map of the body, as shown in FIG. 7.

Figure 8:
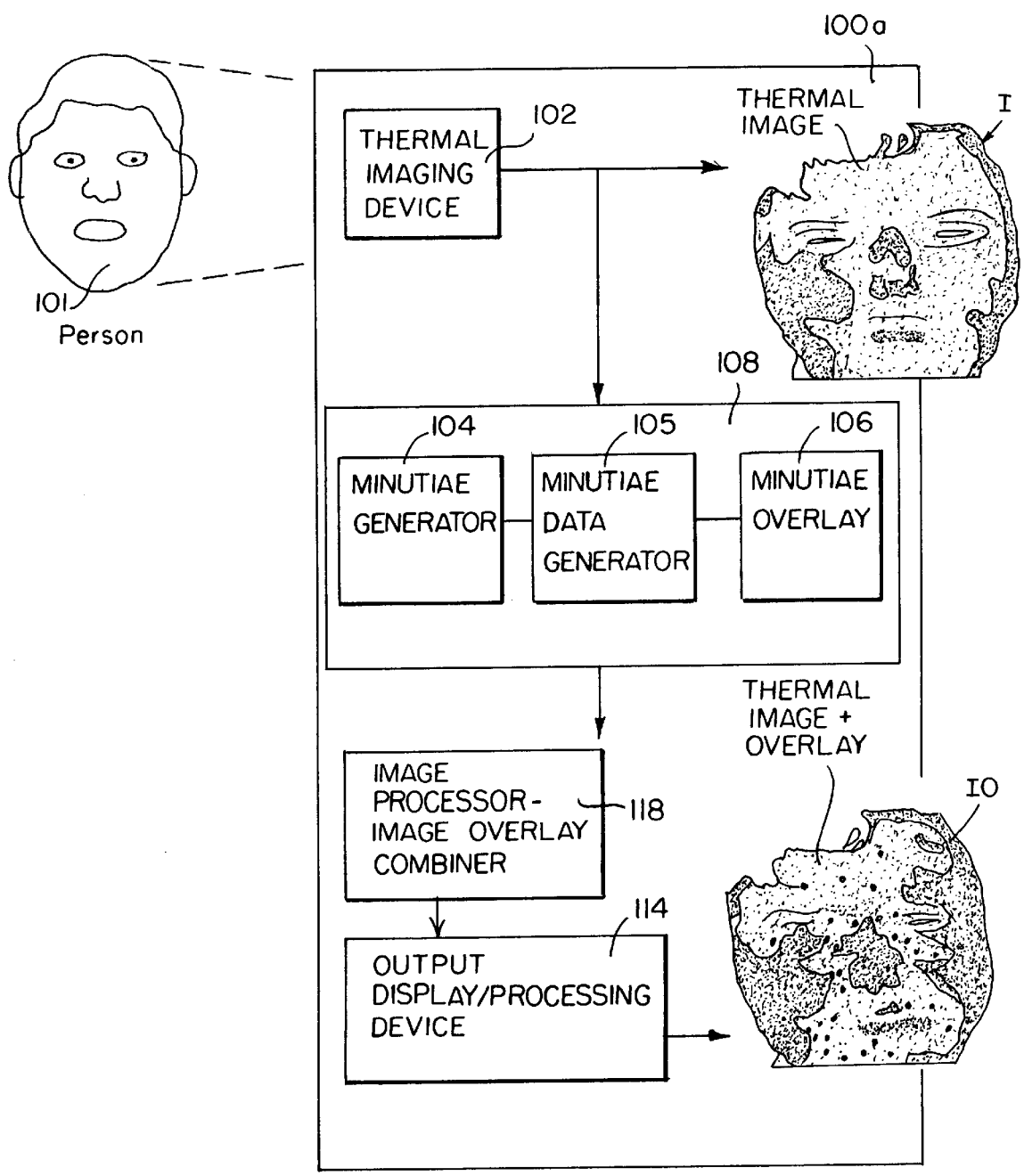
FIG. 8 is a block diagram of the apparatus for annotating an image of the human body according to the invention.

In FIG. 8, there is shown apparatus 100a for processing infrared images to yield repeatable minutiae points corresponding to specific vascular locations under the skin. The apparatus includes a thermal imaging device 102 for producing a thermal image I. A minutiae generator 104 and minutia data generator 105 are part of the program memory 108 as is a minutiae overlay device 116. The set of minutiae obtained from any extended are of the body is unique to each individual. In particular, facial minutiae are unique between identical twins. The same thermal minutiae are repeatedly extracted from a given individual. They are overlaid by the overlay device 116 and annotated by an image processor 118 on the infrared image or on a visual or any image obtained from another medical sensor having the same orientation to the subject. From the processor, the annotated image signal is delivered to an output display/processing device which produces the thermal image with overlay IO.

Figure 9:
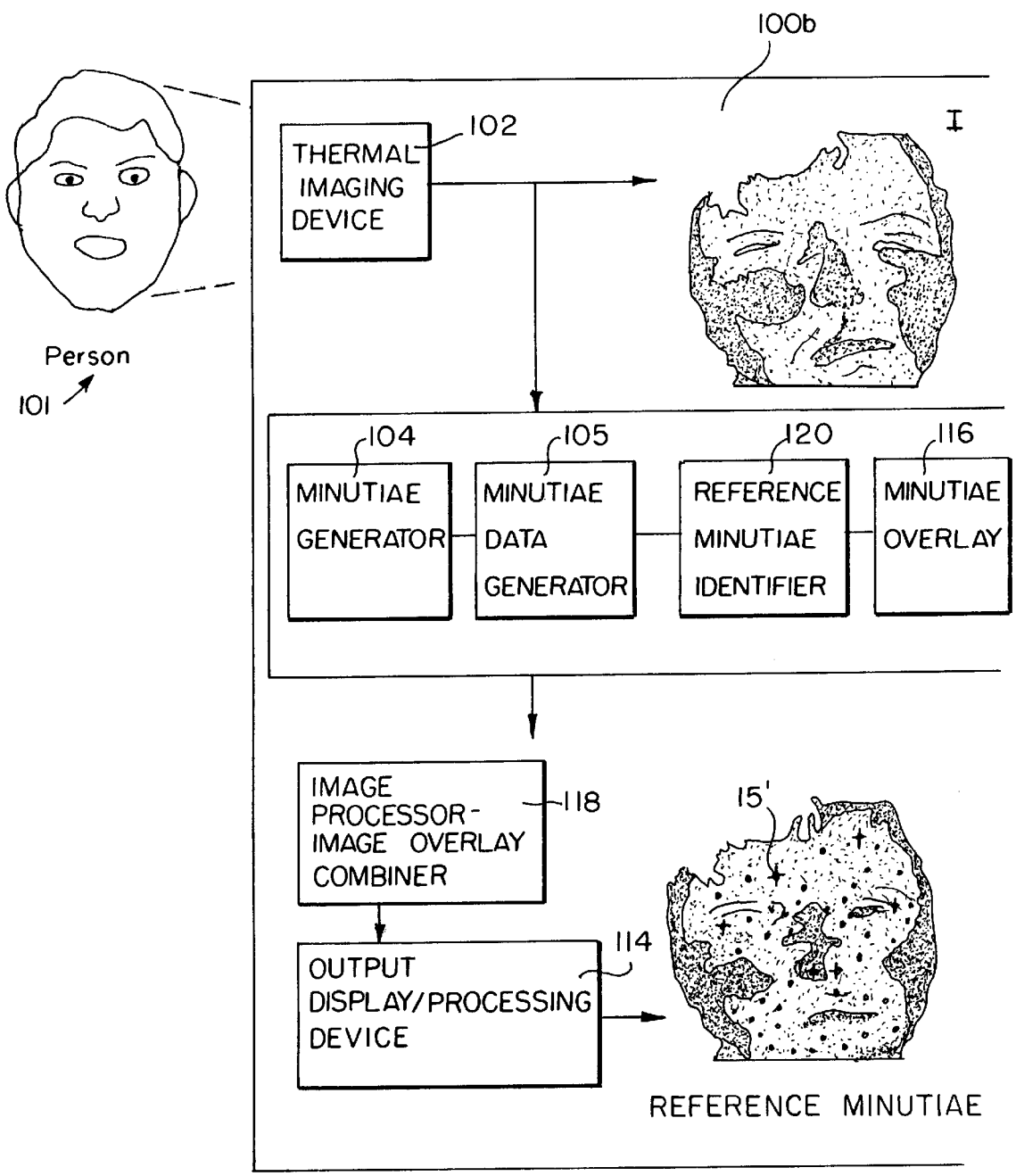
FIG. 9 is a block diagram of a modified apparatus of FIG. 8 for identifying reference minutiae in an annotated image.
Figure 10A:
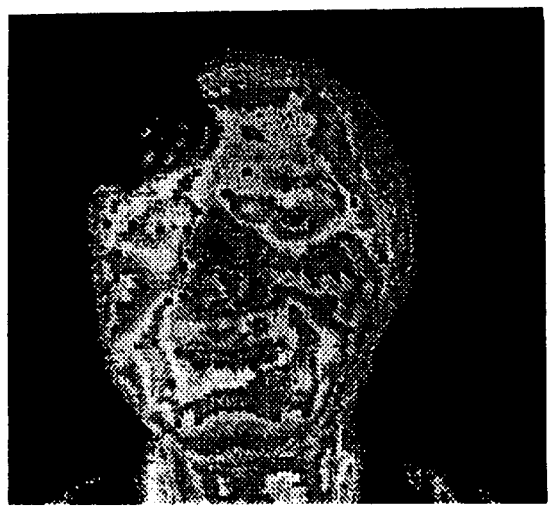
FIGS. 10a, 10b, and 10c illustrate facial minutiae superimposed on three different thermal images, respectively, of the same face.
Figure 10B:
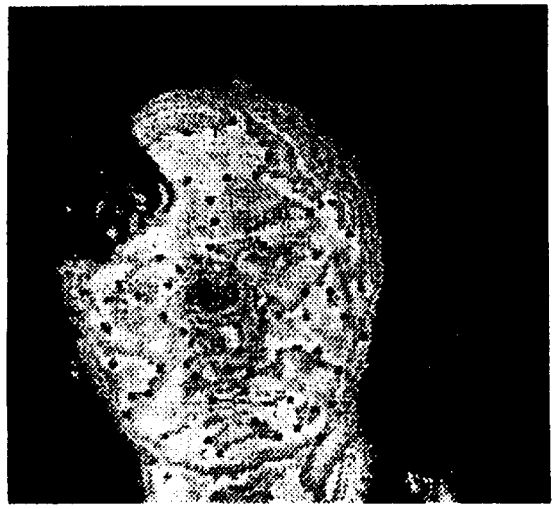
Figure 10C:
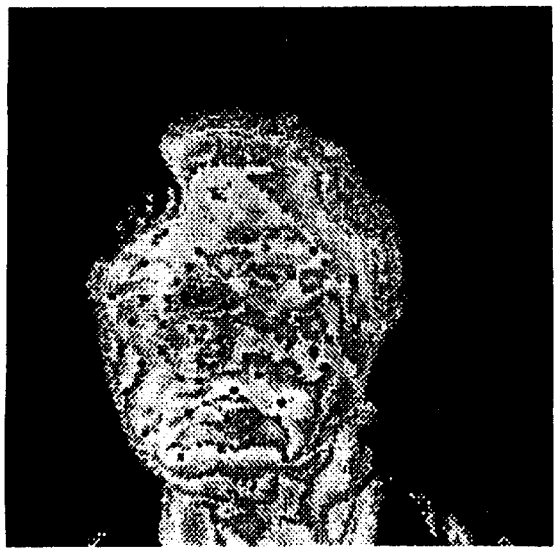

In FIG. 9, there is shown a modified apparatus 100b to that of FIG. 8, wherein a reference minutiae identifier 120 is provided between the minutiae data generator 105 and the minutiae overlay device 116 to identify and specify reference points 151 in the thermal image and overlay IO. The reference points allow manual or automated comparison, merging, or registration among a set of images taken at different times with different orientations or different medical instruments. FIGS. 10a–c illustrate minutiae automatically extracted from a facial thermogram as the head turns. Current infrared cameras commonly produce 30 frames of video output per second, and minutiae extraction and annotation can be performed in real time as those frames are generated.

Figure 11:
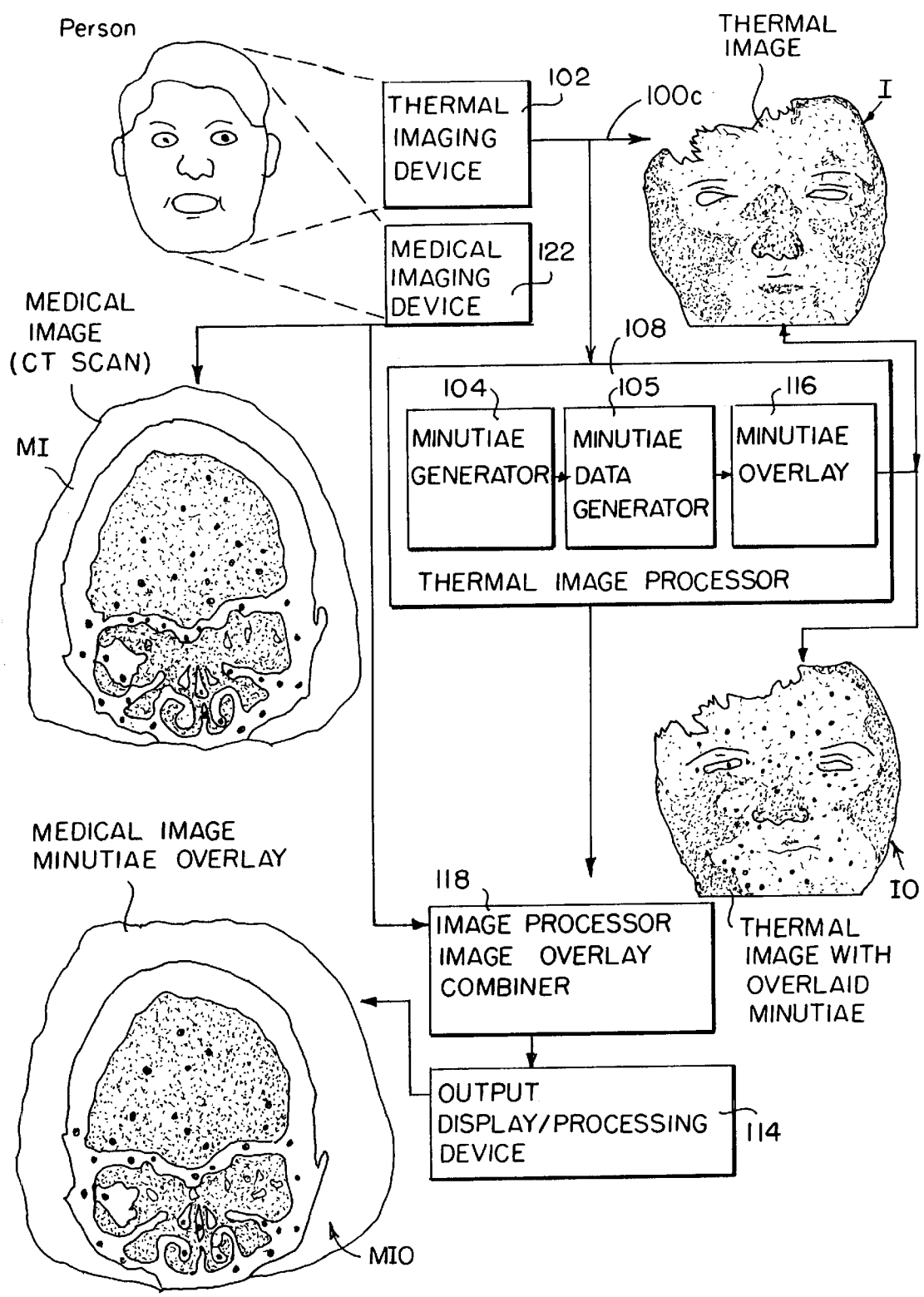
FIG. 11 is a block diagram of an apparatus for annotating a medical image of the human body according to the invention.

FIG. 11 illustrates alternate apparatus 100c for generating a medical image MI of a portion of the body via a medical imaging device 122 such as an x-ray machine. The medical image can be annotated with a minutiae overlay to generate a medical image with minutiae overlay MIO from the output display/processing device.

The inventive technique differs from visible recognition approaches in that it does not merely sample a finite number of points on an image; it extracts points which have particular meaning. This provides increased resolution at the same time it reduces the degree of computation required. The essential features of the technique are the uniqueness and invariance of thermograms, the use of a passive imaging technique to obtain subsurface details, the use of automated minutiae extraction to match different images taken of the same individual, and the use of standardized minutiae locations to compare different persons or the same person as he grows from childhood to adulthood. The matching technique involves developing sets of corresponding points in two images, morphing one image into the reference, and measuring the degree of morphing as an indicator of the amount of difference. Similar automated procedures are then used to verify that imagery is from the same patient, identify a patient by comparison to a database of images, and compare images taken at different time and/or with different sensor modalities.

The minutiae extraction and annotation procedure locates the position of each minutia. In addition, it may note characteristics of each point such as a vector indicating the orientation of the corresponding blood vessel, a second vector indicating the relative orientation of the branching blood vessel, normalized apparent temperature measure, and apparent width of the corresponding blood vessels. As with some of the fingerprint minutiae matching machines, use of the characteristic data can enhance the speed and accuracy of identification. Furthermore, it can improve the accuracy and speed of automatic fusion of medical imagery.

This basic technique can be employed on an area-by-area basis when portions of the body cannot be seen or when significant changes have occurred in portions of the thermogram such as when portions of the body have suffered external wounds. This would be done by segmenting the thermogram to consider only the portions of the body in which the minutiae can be detected. Functionally, this is equivalent to matching a latent partial fingerprint found at a crime seene to a full rolled print filed in the FBI system. The set of minutiae points, together with characteristics which describe each such point and its relation to other minutiae is considered unique to the individual and persistent, for both contact fingerprints and thermal minutiae.

Verification that two medical images are from the same person can be an end goal in itself or the first step in further processing the two images to extract comparison data. Telemedicine applications, electronic filing systems, insurance claims processing, updating of medical records, and extraction of medical histories during emergency treatment are some of the situations in which it is essential to have a reliable, fool-proof method for positive identification of the subject and precise localization of imaged areas.

The use of infrared identification (IRID) has several advantages over other methods for recognition of persons. IRID operates regardless of lighting conditions. It requires only a single frame of imagery, taken in 1/30 of a second, for positive identification, and so can provide on-the-fly recognition during emergency admissions or evacuations. This imagery can be collected at a distance, without causing a delay or inconvenience to the subject. No parts of the system come into contact with the subject. Since thermal images are essentially immune from variations caused by illumination and shadows, it is not necessary to control those variables. IRID provides continuous identification and confirmation verification of ID even in the dark. A cheaper, cruder form of thermal imaging can be obtained from use of heat-sensitive crystal sheets, which require contact with the skin. More expensive, active imaging of the vascular system can be obtained from laser doppler. Either of these could be the source imager for extractions of minutiae; however, the operational advantages of passive thermal imagers make them the preferred sensor.

Thermal minutiae can be obtained from commercially-available thermal imaging devices sensitive in the 3 to 5 or 8 to 12 micron wavelength bands. Images are this type are shown in FIGS. 7, 10, 12, and 13.

Current infrared cameras produce a standard analog or digital output providing 30 frames per minute as shown in FIGS. 7–10. Tracking the minutiae from frame to frame assists in the exploitation of the dynamic IR imagery by allowing measurements to be made over time from the same body locations while accommodating changes in position due to respiration, voluntary or involuntary movements of the subject, and intentional or accidental variation in the position of the imaging system. The use of infrared video imagery also allows the imagery to be recorded in real time for later analysis, and provides a self-documenting chain of custody identification of the person recorded, all without the necessity for the cooperation of the person being imaged.

Infrared imaging can be used to locate minutiae points over the entire body surface which correspond to intersection points and branch points of the underlaying blood vessels. This provides a built-in set of registration points on the body's surface, which can be annotated onto images produced by any medical sensor used in conjunction with the thermal imager. The registration points then can be used to compare and combine medical images taken with different equipment at different times and under different conditions, facilitating comparison of those images. Also, the minutiae points provide reference points for continuous re-alignment of surgical instruments, radiation sources, and other diagnostic or treatment equipment. Since the infrared camera is totally passive, it can be used continuously during other medical procedures to overlay precise registration points on the other images while also monitoring for overheating, shock, hyptothermia, renal failure, and other medical conditions. At the same time, the pattern of minutiae points superimposed on each image provides positive identification of the patient. Such applications are of particular importance during telemedicine procedures.

The normal body is basically thermally bilaterally symmetric. Side to side variations are typically less than 0.25 degrees Celsius. This fact is used in assigning axes to the body's image. Where the skin surface is unbroken, there is gradual variation of temperatures across blood vessels, with the highest temperatures across the body surface being directly on top of major blood vessels. Major thermal discontinuities occur at entrances to body cavities such as the eye sockets, nostrils, or mouth. These provide global reference points for automatic orientation of the thermal image. Local and relatively minor discontinuities in the skin surface occur at scars, moles, burns, and areas of infection. The thermal surface can be distorted through pressures and activities such as eating, exercising, wearing the tight hats and other clothing, sinus inflammation, infection, weight gain and loss, and body position. However, the minutiae points remain constant with respect to their position relative to the underlying blood vessels.

The technique for thermal minutiae extraction and matching can be summarized as follows:

1. Current thermal image is digitized.
2. Current image is divided into pixels, where the size of the pixel relates to the resolution of quality of the result desired.
3. Certain pixels are selected as minutiae points.
4. Each minutia is assigned a vector having magnitude and directional information in relation to the surrounding characteristics of the thermal image. Additional characteristics, such as type of minutia may also be recorded for each. Typically for each whole body thermal image, there would be on the order of 1200 minutiae.
5. Set of minutiae vectors of the current image are compared by computer to the set of vectors of other images.
6. Comparison results are used to determine corresponding minutiae from the two images, and to morph or mathematically adjust one image with respect to the other to facilitate comparison.
7. Differences between the current image and database images are computed for either the entire image or for areas of interest.

It is desirable that all thermal images in a database be normalized to a standard thermal range and be scaled to a standard size during search and comparison procedures. Both normalization and scaling eliminate some minute amount of identifying characteristics of a particular person or his condition. However, the standardization procedures greatly aid in the exploitation of the database by reducing the need to calibrate every imaging sensor used to produce images which will be filed in, or compared to database images. For example, in accident triage with no accurate ground truth reference in the scene and possibly use of inferior quality imagers, standardization to constant size and thermal range is appropriate in order to match against database. Furthermore, standardization facilitates use of simulated imagery for telemedicine and telesurgery applications. For example, when incorporated into the military's automated battlefield medical pod, real time normalized thermal minutiae can be used to properly position injections and application of external pressure to stop bleeding.

In addition, standardizing database images facilitates comparison of imagery during growth from childhood to adulthood, compilation of medical libraries of images from large number of people, and automated comparisons of current imagery against the base libraries for diagnostic purposes. Standardization to a common use of thermal minutiae would also provide a common reference for comparing images obtained from different sensors which produce different resolution images.

There is great utility to maintaining a summary medial record which could be carried in encrypted form on a small token or card. It would include important medical history information, and would provide linkage into database holding more complete information. The use of thermal minutiae can be of assistance, since it provide a standarized technique for segmenting the complete body, using the thermal minutiae as nodes on a grid of finite elements. The resulting cells in the grid would be coded based upon the compilation of all medical history data relating to that area of the body, and compared against the standardized imagery and status of the corresponding cell in reference model. If there were no entry throughout the medical record for any imagery, diagnostics, treatment, or injury involving that area of the body, or no significant deviation from the reference model, there would be not data for the cell. If a known standard condition involving that area were known, then the standard code for that condition would be entered. Other codes would pertain to unknown conditions, continuing treatment, previous conditions successfully treated, etc. Conditions which are not localized, such as high blood pressure, would by convention by assigned to specific cells within the body outline.

The identification techniques set forth herein can be used to diagnose and monitor treatment for burn victims, for stroke diagnosis, and in telesurgery and telemedicine.

Blood vessels that carry nutrients to the skin are destroyed when tissue in burned. A high powered laser can be used to remove the burned skin, leaving the healthy skin intact. Laser light is differentially absorbed and reflected by live and dead skin, such as in the area of a burn. Certain dyes such as indocyanine fluoresce when in contact with laser light and can be injected into a patient's blood to indicate healthy tissue. Alternately, an IR imager can be used to indicate dead skin vs. healthy skin, since the dead skin appears relatively cold as a result of having no functioning blood vessels. More than 100,000 person per year in the US alone suffer severe burns. The total cost of treating these patients exceeds $2 billion. Treatment includes massive transfusions to replace the blood lost during surgery to remove dead skin. Blood loss is the main cause of death in burn patients. Continued heavy bleeding often prevents a successful skin graft after the burned skin is removed.

Ideally performed, laser ablation kills a 100 micrometer-thin layer of skin below the burned area. Due to the thinness, nutrients can still get through; however, the layer stops the bleeding from preventing a good graft. IR minutiae can be used to reposition the patient, monitor healing in specific areas, compare various salves, dressing, etc. used, and re-photograph the person, achieving standard imaging results regardless of the skin tone of the patient.

Figure 14:
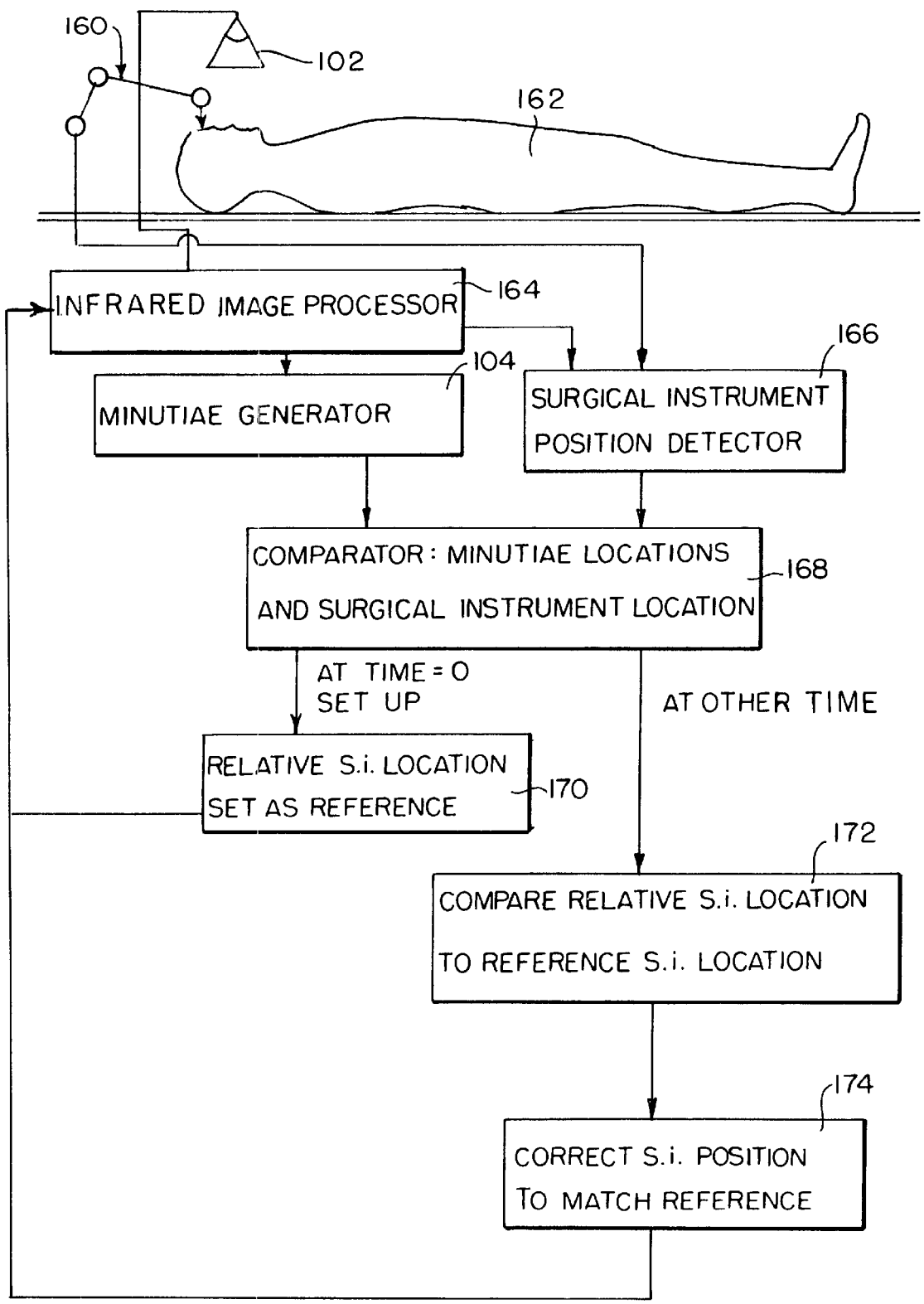
FIG. 14 is a block diagram representing apparatus for maintaining the position of a surgical instrument relative to a surgical site according to the invention.

Referring now to FIG. 14, there is shown an apparatus for maintaining the position of a surgical instrument 160 relative to a surgical site in a patient 162 during a surgical procedure. A thermal imaging device 102 such as an infrared camera, generates a thermal image output to a minutiae generator 104 to identify minutiae in the vicinity of the surgical site. As described above with reference to FIG. 9, a reference minutia pattern is also generated for a statutory patient. A surgical instrument position detector 166 senses the position of the instrument and produces an output signal corresponding therewith. The minutiae pattern for the patient and the surgical instrument positions signals are delivered to a comparator 168. The relative position of the instrument to the surgical site is set as a reference at time 0 at 170. Displacement of the patient and/or the instrument with respect to the reference at times other than 0 is detected by the comparator which can produce an output 172 used to reposition the instrument via a device 174 for proper orientation to the surgical site.

Each year, 500,00 American have strokes and 150,000 of them die, making stroke the third leading cause of death, and the major cause of disability among adults. In the near future, new drug therapies may be able to return blood flow to stroke-damaged (ischemic) tissue, protect it from permanent damage, and promote recovery of function. However, the primary care physician must be able to characterize the patient's acute neurological injury precisely enough to guide laboratory assessments and treatments. Stroke is a heterogeneous group of conditions with many causes, levels of severity, and clinical presentations.

Identifying the point of stroke damage and the extent of damage depends on a pattern of normal and abnormal findings. Computer tomographic (CT) findings often are normal during the first hours after ischemic stroke. Also, abnormalities found with neuroimaging may be unrelated to the patient's acute problem. Further confusing the situation, seizures, tumor, and intercranial hemorrhage can mimic stroke. Treatment with anticoagulants or experimental clot-dissolving agents would be contraindicated in patients with hemorrhage but could be of value in some patients with ischemic stroke.

Continuous IR monitoring of the patient can possibly assist in detecting and tracking minute variations in blood flow patterns associated with the onset, location, and severity of stroke; and also associated with reaction to drugs and other treatments.

Within the next 10 years, both military and civilian medicine are expected to make routine use of telesurgery where the patient and surgeon are not co-located. It is estimated that 90% of the information a physician needs to know about a patient can be acquired and brought to him electronically. In laparoscopic surgery today, a surgeon looks only at video images without looking at the real organs at all. Dermatology and pathology are both already using electronic images as well as x-rays and medical records. Laparoscopic surgery is an electronic form of surgery. Teleradiology, telepathology, and teleconsulation are already widely accepted electronic medical practices.

As telemedicine and telesurgery become more common, there will be more potential for error in identification of patients and the treatment to be performed, and more need to document the precise medical history and treatment procedures performed by a given doctor on a given day. Filing, recall, and comparison of documentation collected over time by different sensors at different facilities will need to be automated to a greater degree, while protecting the privacy of the patients. The identification technique of the invention offers a low-cost, repeatable, non-invasive, passive system for standardization and registration of many current forms of medical imagery, while also offering an approach to high security maintenance of files with immediate access in emergency situations.

Identification of Drug and Alcohol Usage

Figure 16:
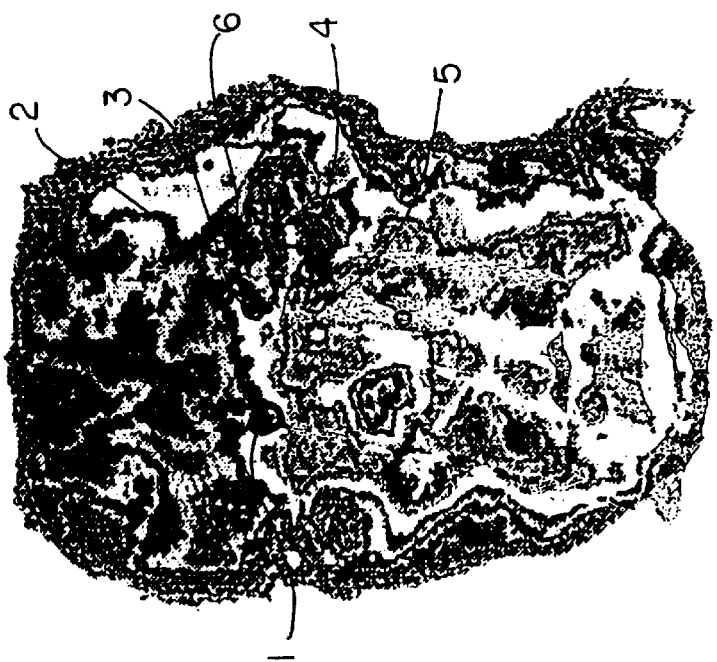
FIG. 16 is a facial thermogram of the individual of FIG. 15 under the influence of alcohol.
Figure 15:
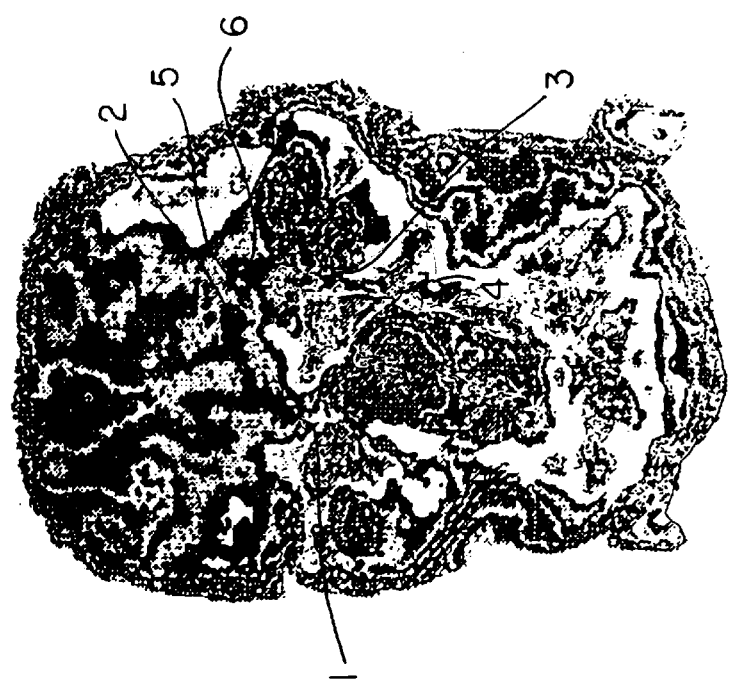
FIG. 15 is a facial thermogram of an alcohol-free individual.

Many drugs, including cocaine and alcohol, are vasoconstrictive substances which cause cooling of the skin surface, the resultant cooling is detected through passive imaging of the thermal energy emitted form the face. In FIG. 15 is shown the thermal image of an individual who is substance free and in FIG. 16 is a thermal image of the same individual after the ingestion of alcohol.

The thermal imaging techniques of the present invention can be used to detect substance use by individuals, even where the individual's identity is unknown. This is accomplished by compiling databases of statistical analysis of thermal signatures obtained from clinical trials in which cooperating subjects have concurrent drug testing performed using urinalysis or blood testing along with thermal signatures obtained from known subpopulation but without concurrent testing by other means.

The vascular system supplying the human face typically exhibits thermal variations on the order of 7° C. across the facial surface. Certain general features, such as hot patches in the sinus areas, relatively cool cheeks, and cold hair pertina to all facial thermograms. Other features such as specific thermal shapes in certain areas of the face are characteristic of a particular person. Measured disturbances to other features, such as the general symmetry between two sides of a face, range of thermal variations in the forehead, peak temperature, size of canthi pattern, and variations in those disturbances over time, may be correlated with a high probability of drug or alcohol use.

Variations in temperature across the facial surface can be imaged by thermal cameras sensitive to wavelengths in the 3–5, 8–12, or 2–15 micron ranges. Current cameras can provide thermal resolution better than 0.07° C. and spatial resolution of better than 0.02", resulting in 65,000 to 265,000 discrete thermal measurements across the surface of the face. For most such cameras, that thermal map is generated 30 times per second to produce either a standard video output which can then be recorded and processed on standard videotape equipment, or a direct digital signal which can be immediately input to a computer.

Certain drugs appear to produce characteristics features in facial thermograms, which may be identifiable from detailed analysis of the structural patterns and distribution statistics. Furthermore, the rate of change at any point in time may be a discriminator between chronic and recent use of each drug. Using currently available thermal imaging cameras, thermal signatures emitted from the face can be used to deduce changes in activity levels of specific arteries in the brain which are known to be affected by particular drugs.

Figure 2B:
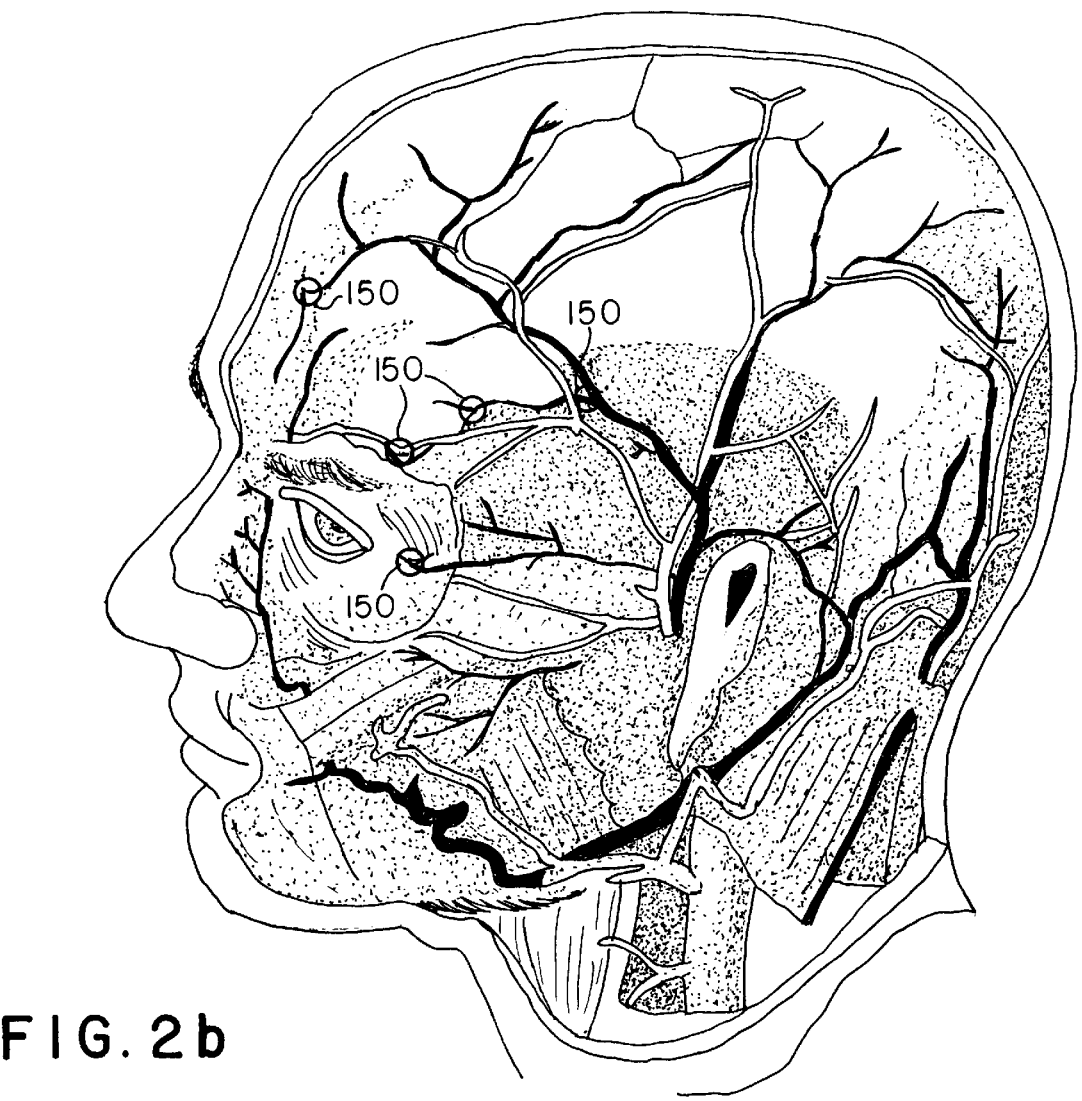
Figure 3:
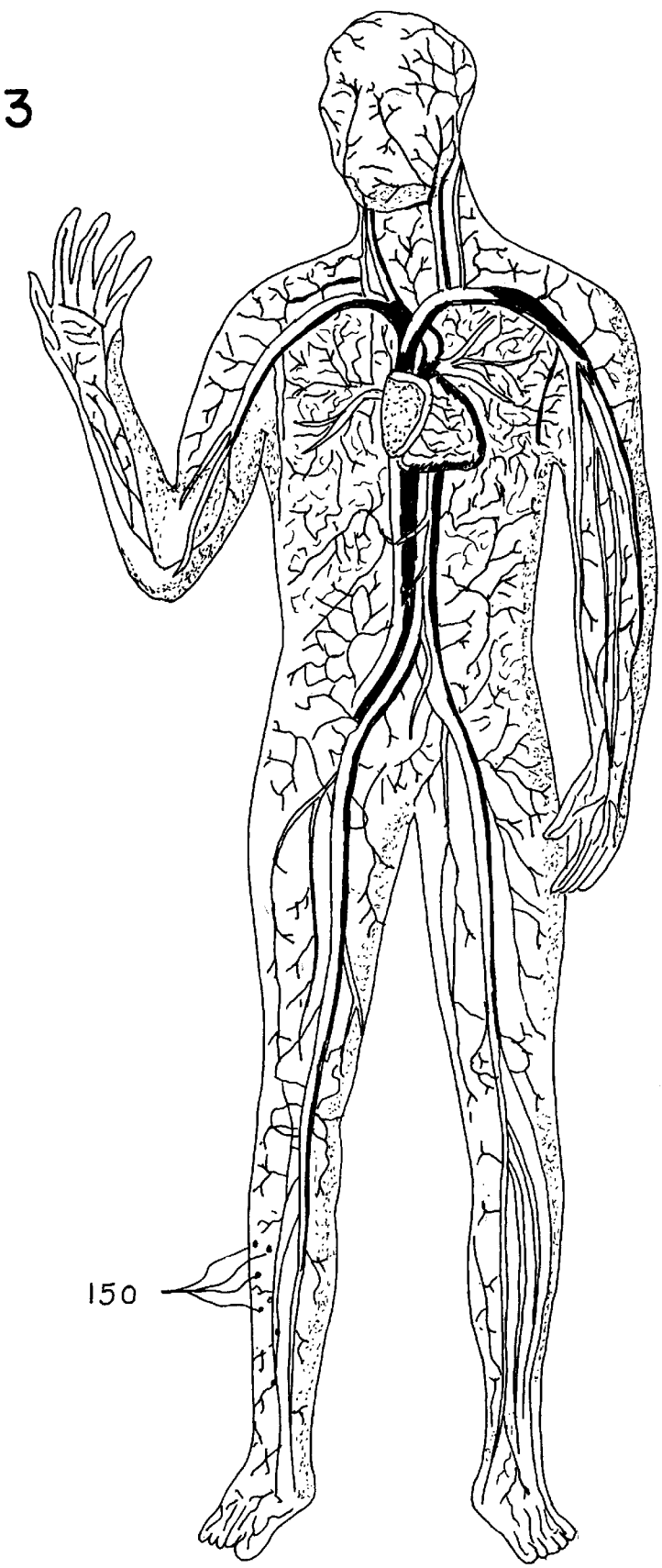
FIG. 3 is a front view of the human vascular system illustrating the location of thermal minutiae therein.

The vascular system has a common structure in each person, with known pathways for instance from the heart to the brain, and known pathways between blood vessels in the face and those in the brain as shown in FIGS. 2b and 2b. Using the SIMCOS technique, a set of standardized minutiae appearing in the face can be identified. Through clinical drug trials using known types, amounts, purity, and administration techniques, the thermal effects over time at each such minutiae location can be observed. The effect of varying the type, amount, or purity of drug can also be observed. The effect on different people can be observed. Since the thermal effects may be quite small and localized, it is important to utilize the SIMCOS method for identifying the precise minutiae locations in each subject. That provides repeatability of measurements over time without requiring the application of registration markers to the face, or the use of invasive techniques to repeatably find the same locations. Also, it provides a method for comparing corresponding locations in different subjects.

Figure 17:
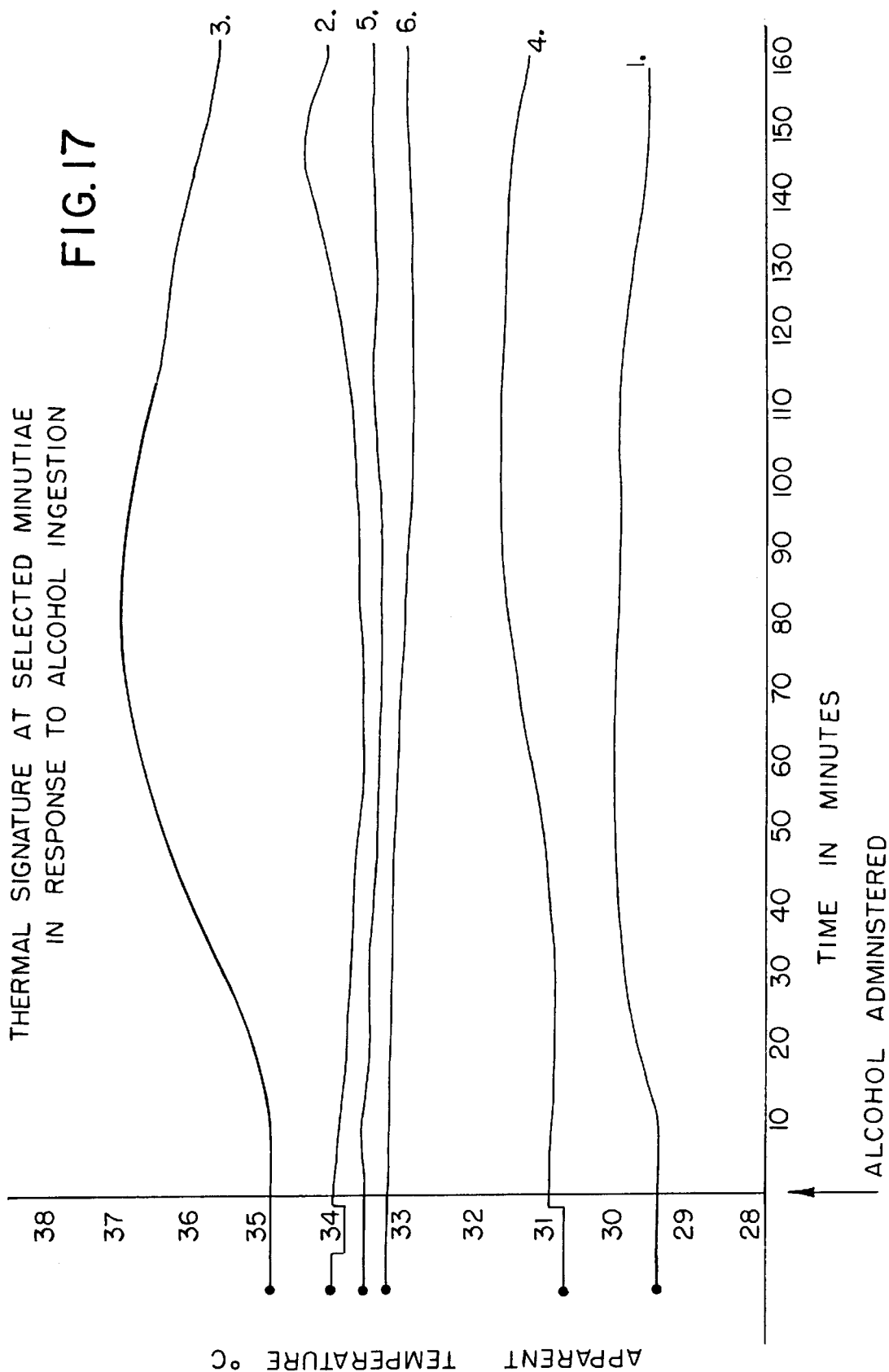
FIG. 17 is a graph representing the thermal signatures of selected minutia points of an individual prior and subsequent to use of alcohol.

Statistical analysis of time-varying thermal signatures at each facial minutiae point before, during and after drug or alcohol administration provides a reference dataset which represents the thermal effect of that substance under the protocol used. A library of thermal minutiae substance effect signatures can be developed for various drugs and other substances for which screening is desired, including for prescription and over the counter medications, tobacco, and alcohol. FIG. 17 presents an illustration of thermal signatures associated with substance-free subjects. These may differentiate between sex, age, size, medical history, or other characteristics of the substance-free subjects. In addition, thermal minutiae on non-substance signatures may be developed for each person enrolled in to a system who will be subsequently scanned for substance use. At the time that the thermal data is collected, urinalysis or blood testing can be performed to assure that the subject is substance-free.

Subsequently, each time a person enrolled in the system is scanned, the same facial thermal minutiae are located and the corresponding thermal signatures computed. They are compared against that subject's own substance-free thermal signatures. If there is sufficient match, no further analysis is required. Otherwise, the thermal signatures are compared against the library of substance effect signatures. If there is sufficient match, the system provides an output to the system operator that a potential substance detection has occurred.

If desired, relevant data from the system may be transmitted to a medical review officer for a final determination. Such data could include the current thermal imagery of the person's face, reference imagery from the database taken of the same person when he was known to be substance-free, the thermal signature calculations which lead to the system's determination of a possible substance detection, the library reference thermal signature which was used by the system to make that determination, the system's calculated confidence in the determination, thresholds which were set by the system manager relative to the infrared camera sensitivity and other system factors, medical data on file about the person including known or self-reported use of prescription or over the counter medication, or a past history of substance use. The Medical Review Officer determines whether to accept or override the system's determination, or specify that further testing such as urinalysis is to be performed.

The technology of this patent involves clinical studies in which known amounts of controlled substances are administered to subjects whose thermal images are monitored and stored to provide archival references. Analysis of those images is used to determine the time-varying thermal effect of specific drugs at specific minutiae sites on the face, which are specified by anatomical landmarks. After an individual ingests a drug, changes in his or her thermal signature gradually occur until a thermal "climax" is reached after which the signature gradually returns to its normal state. In chronic drug users, permanent physiological changes may occur such that there is no longer a smooth total decay of the apparent drug-induced effects. By processing a significant number of thermal images, thermal signature markers are identified and related to standardized vascular system locations whose thermal variation are highly correlated with use of the particular substances. References may be developed for an individual, for a class of individuals grouped by age or other characteristic, or for a general population.

A general determination of substance-free vs. substance-influenced classification may be based upon data collected on the thermal effects of various substances of interest. In addition, certain substances produce characteristic results which may be identifiable from detailed analysis of the thermal signatures associated with facial minutiae, and/or with distribution statistics from those signatures. Furthermore, the rate of change at any point in time may be discriminator between chronic and recent use of each drug. Techniques for processing sequences of thermal images may enhance the visibility of bilateral asymmetries, anomalous static conditions, and unusual time-varying trends in the thermal signatures associated with specific minutiae locations in the face to indicate activity levels of specific arteries in the brain which are known to be affected by particular drugs. Therefore, when a substance is known to affect particular functions, vascular pathways to the corresponding brain areas should be analyzed for related thermal signatures at minutiae points along the pathways, under the assumption that increased activity at the brain site will be found to correlate with increased vasomotor activity along pathways leading to that site, as evidenced by thermal changes.

In order to best compare images from different people and under different conditions, facial thermograms must be standardized and registered to common coordinates. The preferred approach is to use the standardized infrared minutiae coordinate system (SIMCOS) technique which locates standard minutiae points on each facial thermogram. In its preferred embodiment, the SIMCOS minutiae correspond to anastomoses which are connections or branchings of major superficial veins and arteries in the facial area. Approximately 175 such points exist in the face. A subset of the SIMOS minutiae which relate to blood vessel or areas of the face affected by a particular substances is selected. The substance activist at the brain site will be found to correlate with increased vasomotor activity along pathways leading to the site, as evidenced by thermal changes.

The collection of differences between the time-varying thermal signatures for the substance-active minutiae, compared to the collection of time-varying thermal signatures for the same points in the absence of the substance, represents the marker for that substance. For each substance of interest, a marker may be developed for a particular individual, for a class of persons grouped according to some criterion, or for a more general population. The substance-free marker can likewise be developed for a particular individual, class of persons, or general population.

In subsequent screening of a known individual for a particular substance, his current thermal image(s) are analyzed to extract substance-active minutiae which can be seen in the available image(s). The set of thermal signatures is compared to the substance marker collection and substance-free marker collections. Measures of similarity are calculated for individual, class, or general population comparisons for each substance of interest. Various correlation associated with substance use, or with substance-free references in the system library. Normalized temperatures vs. time waveforms for each minutiae can be compared with the corresponding waveform from the reference. The waveforms are slid along the time axis until the best fit is found, since it is not known when, if at all, the person being screened may have used that substance. Another correlation approach involves sampling the thermal waveforms and producing a matrix of values, where one dimension of the matrix is the number of minutiae used, and the other is the number of temperature samples over time. The reference library can include wider matrices, involving longer time period than is practical for an operational screening system. The comparison between the collected matrix and the reference matrix would use a digital shifting and difference calculation to find the best area of match.

A measure of goodness of match is made between the collected thermal signatures and the signatures for each substance under each protocol in the library. The system manager selects a threshold to be applied to each comparison, such that matches which are closer than the threshold will cause the system to issue a notice of possible substance detection.

The results of comparison with the different markers may be recorded or stored or output to decision markers. Alternatively, thresholds may be automatically applied to the calculated differences to render a pass/fail or clean/under-influence determination. The statistical estimate of confidence in the determination can also be presented.

Figure 18:
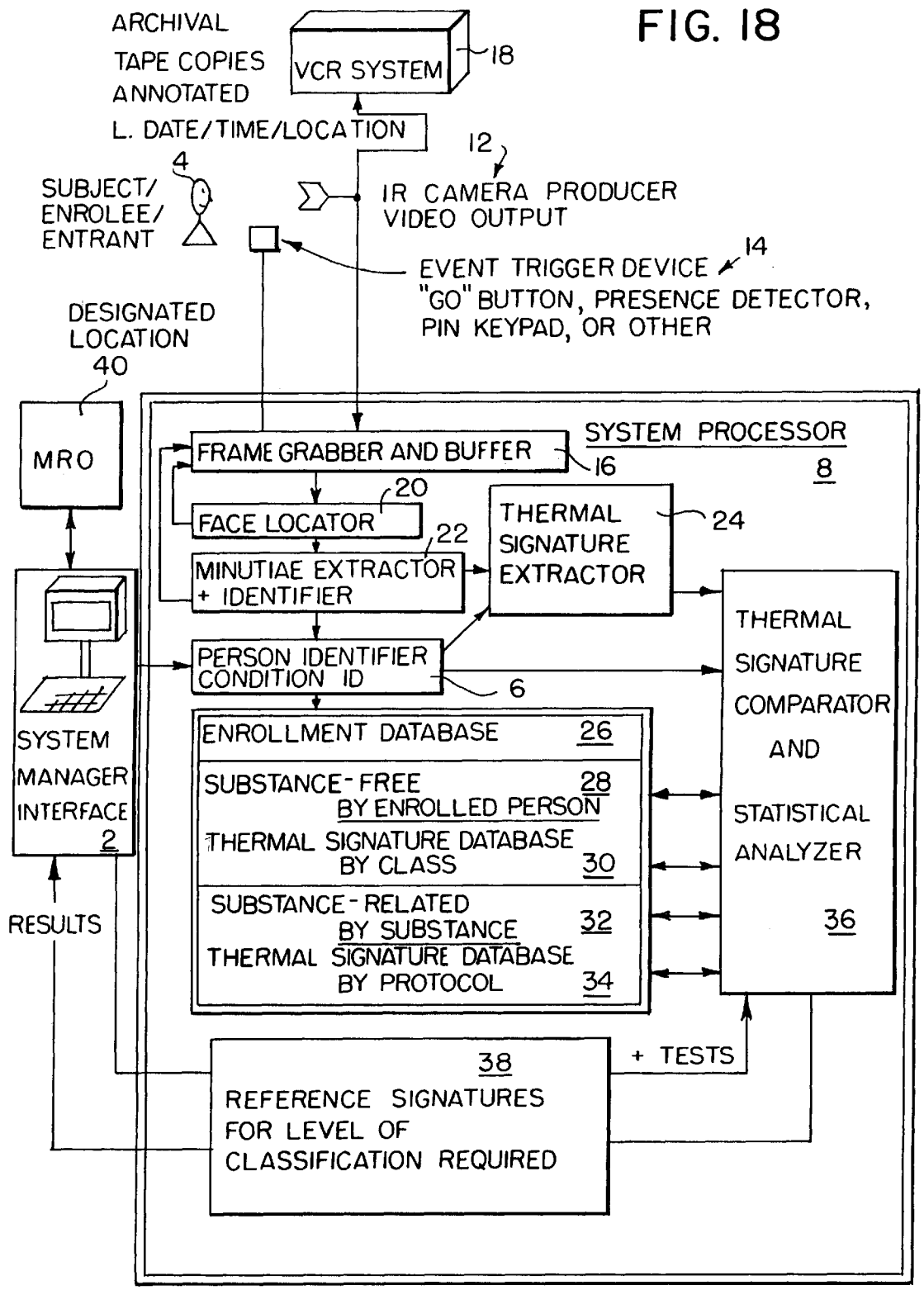
FIG. 18 is a block diagram of the apparatus for detection of alcohol and drug use by an individual according to the invention.

The apparatus for drug and alcohol detection is shown in FIG. 18. Three primary functions are performed with the apparatus. Enrollment, Reference Signatures Development, and Screening. System components may in general be rendered as software, hardware, or firmware elements.

Prior to automated operation of the Identification and Detection (ID&D) system, a human operator termed a System Manager must perform set-up and initialization of the system, which he does via the System Manager Interface, which includes a monitor, keyboard, and possibly a printer and other peripherals such as a mouse which are normally associated with personal computers. A System Manager must confirm the identity of the enrollee 4, and input the associated identification information into the person identifier and condition identifier database 6 within the system processor 8. The enrollee's current and past medical history data is also input to the system, including the results of urinalysis or blood tests to detect substance use, current use of illicit substances, and other information which may bear upon alcohol and drug testing results.

The enrollee stands or sits at designated location facing the infrared camera 12 and within reach of the event trigger 14. When the event trigger is engaged by either the enrollee or System Manager, the output from the infrared camera is sampled by the frame grabber 16 and the resulting frame stored in its buffer. At the same time, the camera output is recorded on a video cassette recorder 18 which incorporates annotation of the date, time, location, and identify of the enrollee.

The image in the frame grabber and buffer is processed by the face locator 20 which determines that the image includes a single face which is in focus and of a suitable size and position. If the image is not suitable according to software criteria established within the face locator, a new image frame is grabbed and the process repeated until a suitable image is obtained.

The image is then processed by the minutiae extractor and identifier 22 which locates the SIMCOS minutiae points and extracts their positions on the image and the corresponding apparent temperatures. Additional frames are grabbed and processed for a period of time selected by the system manager.

The extracted minutiae locations and corresponding temperatures are processed by the thermal signature extractor 24 which generates for each minutiae point the thermal variation over time. For enrollment purposes, a single frame may suffice. However, multiple frames over a period of seconds should be taken in order to help calibrate and factor-out noise in the system.

Personal data about the enrollee is transferred to the enrollment database 26, along with the thermal signatures extracted for the enrollee. If the enrollee is known to be substance-free, the thermal signatures are also transferred to the substance-free signature database 28 stored by enrollee and also to be substance-free thermal signature database stored by classification of enrollee 30.

If the enrollee is known or found to be substance-influenced, the thermal signatures are instead transferred to the substance-related thermal signature database stored by substance and also to the substance-related thermal signature database stored by protocol 34. The definitions of protocols will relate to clinical trial used for developing reference thermal signatures, and may also include self-reporting classifications such as "heavy regular user of cocaine", or "infrequent user of marijuana but not within the past month."

The extracted thermal signatures of the enrollee are also transferred to the thermal signature comparator and statistical analyzer 36 which compares the signatures of the enrollee with other signatures in the databases. If the enrollee's signatures vary too much from the others in the same substance-free class or from others in the same substance-related or protocol-related databases, then the system manager may request review by the medical review officer 38 prior to including the enrollee's data in the database.

If no anomaly is detected in the enrollee's thermal signature, then the enrollee is instructed as to how to activate the system for future access and screening. If a personal identification number is to be used, that PIN will be assigned. If voice recognition, ID card, or other technique for identification is to be used, those procedures will be taught. The enrollee is now enrolled in the system.

The substance use identification and detection system requires databases of thermal signatures from substance-free and substance-related images. During clinical trials in which substances are administered under rigorous protocols, the same apparatus may be used to generate the reference databases.

A clinical trials investigator will serve as system manger. He will perform set-up and initialization of the system, the system manager interface 2, which includes a monitor or other display, keyboard, and possibly a printer and other peripherals such as a mouse which are normally associated with personal computers. The system manager must confirm the identity of the enrollee 2, and input the associated identification information into the person identifier and condition identifier database 6 within the system processor 8. Since the same person may be enrolled several times under various protocols, he is termed the "subject" to emphasize that he may have several separate files within the enrollment database 26. The subject's current and past medical history data is input to the system the first time he is imaged. During each different test involving different substances and/or protocols, the specifies of the protocol used, as well as recent medical data, including the results of urinalysis or blood tests to detect substance use, will be included in the person identifier and condition ID Buffer 6. The contents of that buffer are transmitted and stored with the results of the thermal signature extractor 24.

The extracted thermal signatures of the subject are transferred to the thermal signature comparator and statistical analyzer 36 which compares the signatures of the subject with other signatures in the databases, if any. If the subject's signatures vary too much from the others in the same substance-related or protocol-related databases, then the system manager may request review by the medical review officer 38 prior to including the subject's data in the databases.

The thermal signature comparator and statistical analyzer 36 processes the thermal signature to establish composite signatures or common characteristics which represent each of the databases: substance-free signatures for each person enrolled in the system; and substance-free signatures for each designated class of enrollees, such as: people under age 16, people 17–20, people 21–30, people over 30, cigarette smokers, non-smokers, people taking heart medication, diabetics on insulin, athletes, vegetarians, social drinkers, etc. If a sufficient number of subjects is used, likewise composite signatures or common characteristics will be calculated for each substance in the database of substance-related signatures, and for each protocol.

After the end of clinical trials, frames are extracted from the archival videotapes and used in place of images directly taken by the infrared camera. Each extracted frame is processed by the system, and the thermal signature comparator and statistical analyzer 36 selects the best matching composite signature and classifies the frame accordingly. First, the thermal signature collection of that frame is classified as better matching the composite for all substrate-free trials or the composite for all substance-related trials. Second, if the subject in the frame is judged to be substance-free, the best matching class of database 30 is then selected. If the subject is judged to be substance-related, then the best matching substance of database 32 is selected. Third, in the substance-free case, the system identifies the best-matching enrolled person's signature within the class selected. In the substance-related case, the system identifies the best-matching protocol for the substance selected. Since the true classification of each subject on the video tape is known, the performance of the system in an automated mode can thus be determined, and the error rates associated with the classification can be calculated. Improvements to the system can then be made according to standard techniques for statistical analysis, including the use of neural nets to adjust weightings consideration of the data from certain minutiae more or less than others, normalizing the thermal variations or not, and normalizing time intervals based upon the size or metabolism of each subject.

When those system parameters have been adjusted to maximize the correct classification from the video archives, the resulting reference signatures are stored in database 38 and used to speed the screening of future enrollees during operational use of the system.

An enrolled person seeking entry through the system as an entrant stands or sits at designated location, facing the infrared camera 12 and within reach of the event trigger 14. When he is in position, he activates the event trigger. The output from the infrared camera is automatically sampled by the frame grabber 16 and the resulting frame stored in its buffer. At the same time, the camera output is recorded on a video cassette recorder 18 which incorporates annotation of the date, time, location, and identity of the enrollee.

The image in the frame grabber and buffer is processed by the face location 20 which determines that the image includes a single face which is in focus and of a suitable size and position. If the image is not suitable according to software criteria established within the face locator, a new image frame is grabbed and the process repeated until a suitable image is obtained.

The image is then processed by the minutiae extractor and identifier 22 which locates the SIMCOS minutiae points and extracts their positions on the image and the corresponding apparent temperatures. Additional frames are grabbed and processed for a period of time set into the system by the system manager.

The extracted minutiae locations and corresponding temperatures are processed by the thermal signature extractor 24 which generates for each minutiae point the thermal variation over time.

The entrants's ID is transferred to the thermal signature comparator and statistical analyzer 36, along with the thermal signature extracted for that entrant. The thermal signature comparator and statistical analyzer compares the signatures of the entrant with database of reference signatures 38. The closet reference signature is selected and the entrant is designated to have the same classification. That classification is transmitted to the system manager interface, which may grant access through manual intervention or through automatic control of an access portal. Depending upon the particular classification selected, or the amount of variation between the entrant and the selected reference signatures, the result classification may be sent either automatically or through manual intervention to a medical review officer 40 for a final determination. The entrant's file from the enrollment database 26 is also sent to the MRO to provide background information.

Statistical analysis of drug or alcohol use within a random population is also encompassed by the present invention. This is performed by scanning a crowd and locating faces therein for analysis.

Various standard methods for locating faces in an image frame can be used. A particularly useful approach uses an ellipse detector to find relatively warm ellipses (thermal faces) within a relatively cool background. The ellipse is located within the expected height range for humans, the detected temperature is within the expected range for human faces, and characteristics common to all facial thermograms (hot canthi regions, symmetry of the eyes, nostrils, ears, cheeks, etc.) are not violated. Each detected face in each frame is evaluated to determine if it meets the quality requirements for further processing. Requirements include the facial image being in focus, being large enough to provide adequate resolution of the facial minutiae, being oriented close enough to full face forward and being free enough of blockages including beards, eyeglasses, and intervening obstructions, such that a sufficient number of facial minutiae can be extracted from the facial image. The specific requirements are dependent upon what substances are to be detected, in how small a dose, and after what period of item. Faces which do not meet the quality requirement are not further considered. Those which are qualified are assigned unique tags.

The next frame is then processed and quality faces are detected as above. Each such face is then compared to the faces in the previous frame, or to those faces from the previous frame which are close enough in location that they could be a particular face in the current frame. Matching is performed using the facial minutiae matching method. If a current and prior face are determined to be the same, then they are given the same tag. This process continues with subsequent frames being likewise analyzed. In general, a particular tagged face will move across and then out of the field of view. When the face is no longer seen by the camera, then the thermal signatures associated with each of its minutiae in each of the frames are combined and matched against a reference database for non-substance and substance-related signatures.

Figure 19:
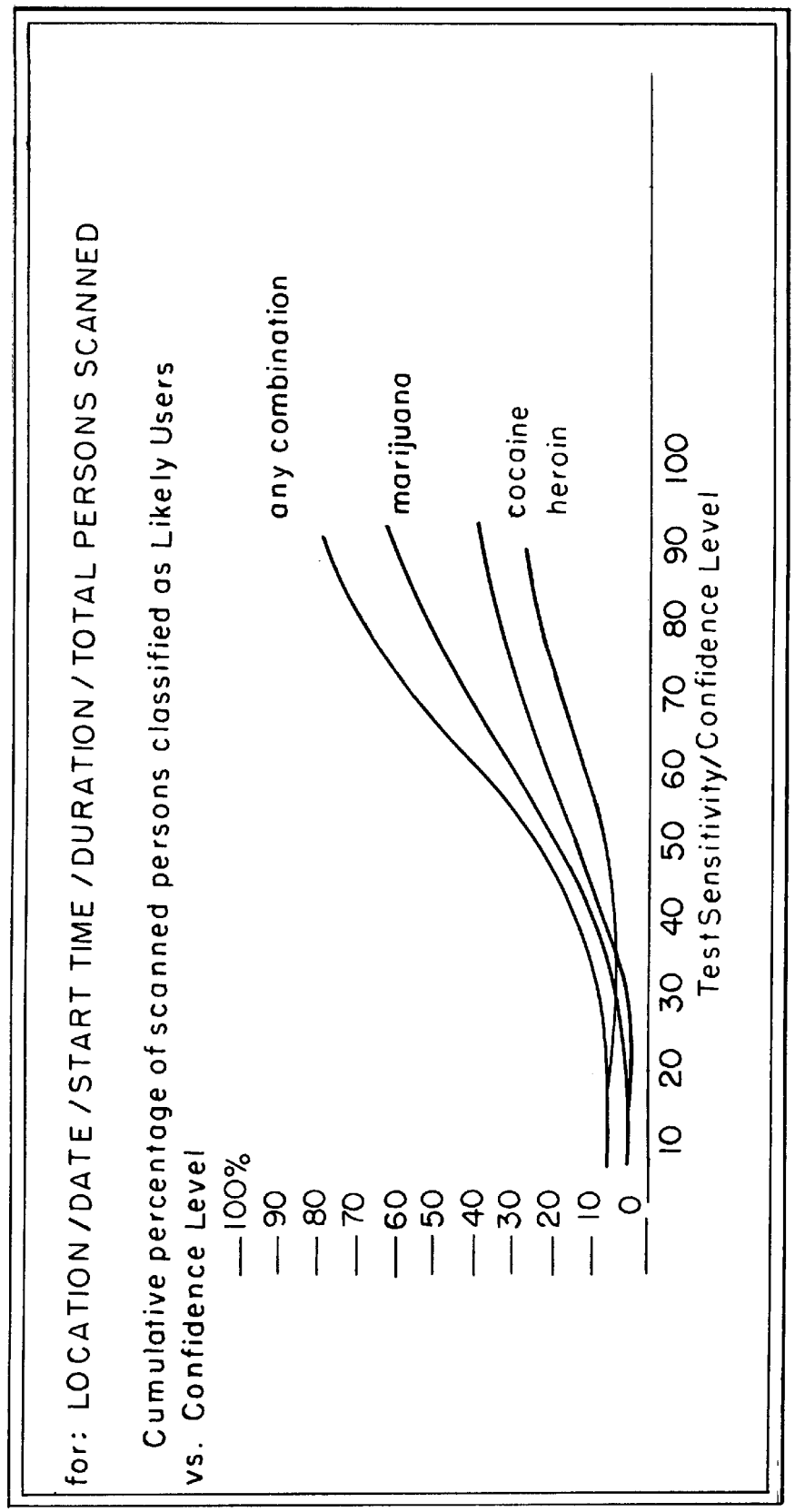
FIG. 19 is a graph representing the results of a statistical analysis of drug users in a random population.

The system is designed for stand-alone operation. IT is deployable for programmable periods of time, during which it will analyze and classify each face which appears within its field of view. The system will not routinely record or store the thermal images, although provisions are made to do that during testing and evaluation of the system in order to allow for improvements to be made in the system and compared with earlier results. The output from the system will be graphical results such as shown in FIG. 19. The cumulative detection index of the y-axis represents the number of people who the system estimates have used marijuana, cocaine, or heroin in an amount and within a timeframe which results in a residual level indicated by the x-axis value at the time of the analysis. The x-axis represents the confidence level of drug signature indication, which is related to the detection precision of the testing and analysis procedures. Separate curves indicate the specific drugs detected, and a composite survey indicates detection of any of the substances. Due to the frequent use of combinations of drugs, the composite curve is expected to be more significant than its components.

The system is tested using known populations of drug users, and its results compared to urinalysis results. The comparison is used to select thresholds for system decisions on classification of thermal signatures. The system can be deployed within a high intensity drug trafficking area, and its results compared to other current estimates of drug usage in that area.

Figure 20:
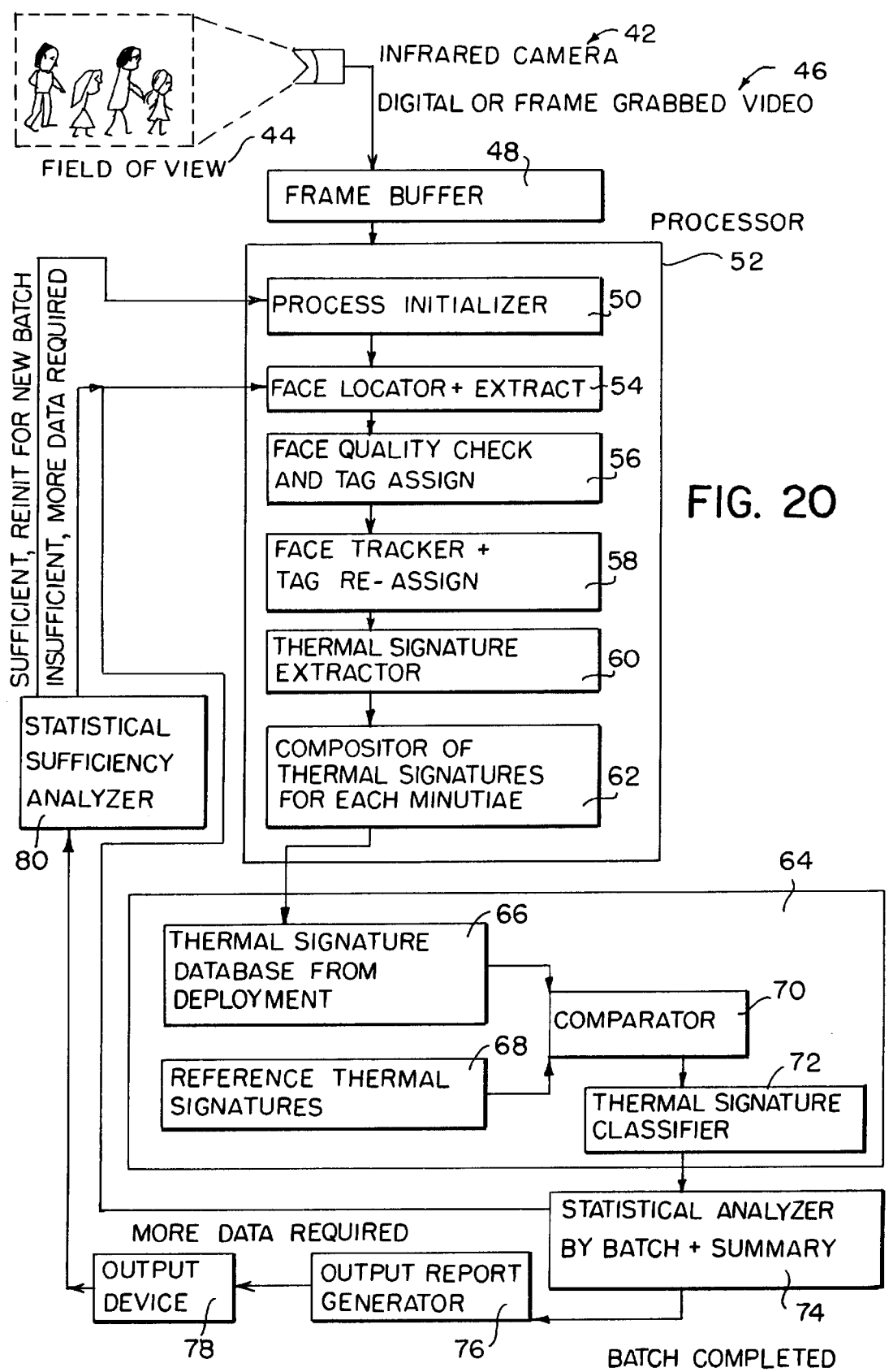
FIG. 20 is a block diagram of the apparatus for detection of alcohol and drug use in a random population.

The apparatus for statistical analysis is shown in FIG. 20. Three primary functions are performed with the apparatus: face acquisition and tagging; face analysis and classification; and statistical population analysis.

An infrared camera 42 is positioned such that persons in the population to be scanned generally enter, transverse, and exit the camera's field of view 44. The infrared camera produces a sequence of frames using either direct digital output or frame-grabbed video output 46, which is stored in the frame buffer storage 48. Processing of the imagery is initiated by an initializer mechanism 50 which may be a proximity detector, motion detector, or other sensor used to detect the possible presence of humans within the field of view.

The system processor 52 is comprised of five components. The face locator 54 applies rules to the buffer stored to identify all faces in the frame. The face quality check 22 applies additional rules to determine if a given face provides sufficient information in terms of focus, resolution, position, and number of minutiae available. Each qualified face is tagged and then compared with qualified faces in the preceding frame, using the SIMCOS technique, to determine which faces have already been seen and tagged.

Faces which are seen in a given frame, may have been temporarily blocked in the previous frames, and so any face may be blocked, turned, or otherwise unqualified part of the time. Comparison against earlier qualified faces is continued for a period of time which is considered a reasonable maximum time for transversing the filed of view. The face tracker 54 reassigns tags so that the same face receives the same tag in subsequent frames. These are two reasons to be concerned about consistently applying the same tag to each face. First, drug and alcohol detection accuracy improves when a face is analyzed for a longer period of time. Second, statistical accuracy improves when each person is counted only one time, regardless of their position or speed, or their being within a group.

Once a face has exited the field of view, the thermal signature extraction processor 60 produces time varying apparent temperature signatures for each facial minutia seen over the course of time of all frames in which that face was seen. The composite thermal signature for that face is produced at 62.

The analyzer 64 of the composite thermal signature compares each imaged person's composite thermal signature to a database of signatures associated with known substances and protocols, or with known subpopulations such as cocaine addicts or alcoholics. More particularly, a signature from a thermal signature database from deployment 66 is compared with a signature from the reference thermal signature 68 is a comparator 70, the output of which is delivered to a thermal signature classifier 72. The analyzer output is delivered to a statistical analyzer 74 for processing the thermal signatures by batch to produce an output summary to the output report generator 76 for the output device 78. A statistical sufficiency analyzer 80 evaluates the report and determines whether the analysis of the population up to that point is statistically sufficient for the intended purpose. If not, additional frames are analyzed. If the analysis is sufficient, then the system is re-initialized by the initializer 50 starting a new collection of faces and leading to a new statistical evaluation.

If the population throughput is well-known, the statistical analyzer 74 can be programmed to run for set period of time before the batch is considered complete and control is passed to the output report generator 76. Other criteria for determining a batch size can be used, including counting the number of tags assigned or the number of detected suspected drug users or the number of detected substance-free persons.

While in accordance with the provisions of the patent statute the preferred forms and embodiments of the invention have been illustrated and described, it will be apparent to those of ordinary skill in the art that various changes and modifications may be made without deviating from the inventive concepts set forth above.

What is claimed is:

1. A non-invasive automated method for continuously controlling the re-aligning the position of an instrument relative to specific locations on a patient's body during a medical procedure, comprising the steps of:

(a) generating thermal images of the patient using a non-invasive imaging device spaced from the patient prior to and during use of the instrument on the patient;

(b) using a minutiae generator to identify minutiae in the vicinity of a specific location of interest on the patient from said thermal image, said minutiae corresponding with specific branch points of blood vessels of the patient;

(c) generating a reference minutiae pattern for a stationary patient;

(d) generating a reference position of the instrument with respect to said reference minutiae pattern;

(e) detecting deviation from said reference minutiae pattern owing to movement of the patient and from said instrument reference position owing to displacement of the instrument; and (f) continuously repositioning the instrument with respect to said reference minutiae pattern to accurately position the instrument for the medical procedure.

2. Non-invasive apparatus for continuously controlling and re-aligning the position of an instrument relative to specific locations on a patient's body during a medical procedure, comprising:

(a) non-invasive imaging means spaced from the patient for continuously generating thermal images of the patient prior to and during use of the instrument on the patient;

(b) minutiae generator means for identifying minutiae in the vicinity of a specific location of interest on the patient from said thermal image, said minutiae corresponding with specific branch points of blood vessels of the patient;

(c) means for generating a reference minutiae pattern for a stationary patient;

(d) means for generating a reference position of the instrument with respect to said reference minutiae pattern;

(e) means for detecting deviation from said reference minutiae pattern owing to movement of the patient and from said instrument reference position owing to displacement of the instrument; and (f) means for continuously repositioning the instrument with respect to said reference minutiae pattern to accurately position the instrument for the medical procedure.

3. A method as defined in claim 1, wherein said imaging device comprises a passive thermal imaging device.

4. Apparatus as defined in claim 1, wherein said imaging device comprises a passive thermal imaging device.

* * * * *